US010232042B2

(12) United States Patent
Bossard et al.

(10) Patent No.: US 10,232,042 B2
(45) **Date of Patent: *Mar. 19, 2019**

(54) CONJUGATES OF AN ANTI-TNF-ALPHA ANTIBODY

(71) Applicant: Nektar Therapeutics, San Francisco, CA (US)

(72) Inventors: Mary J. Bossard, Madison, AL (US); Gayle Stephenson-Phillips, Harvest, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/470,622

(22) Filed: Mar. 27, 2017

(65) Prior Publication Data

US 2017/0196975 A1 Jul. 13, 2017

Related U.S. Application Data

(63) Continuation of application No. 14/819,212, filed on Aug. 5, 2015, now Pat. No. 9,636,412, which is a continuation of application No. 12/296,268, filed as application No. PCT/US2007/008738 on Apr. 6, 2007, now Pat. No. 9,101,670.

(60) Provisional application No. 60/790,339, filed on Apr. 7, 2006.

(51) Int. Cl.

| | |
|---|---|
| *A61K 39/44* | (2006.01) |
| *C07K 16/24* | (2006.01) |
| *A61K 39/395* | (2006.01) |
| *A61K 47/60* | (2017.01) |
| *A61K 39/00* | (2006.01) |

(52) U.S. Cl.

CPC .......... *A61K 39/44* (2013.01); *A61K 39/3955* (2013.01); *A61K 47/60* (2017.08); *C07K 16/241* (2013.01); *A61K 2039/6093* (2013.01); *C07K 2317/40* (2013.01); *C07K 2317/94* (2013.01)

(58) Field of Classification Search

None

See application file for complete search history.

(56) References Cited

U.S. PATENT DOCUMENTS

| | | | |
|---|---|---|---|
| 4,732,863 | A | 3/1988 | Tomasi et al. |
| 5,169,627 | A | 12/1992 | Cunningham-Rundles |
| 5,672,662 | A | 9/1997 | Harris et al. |
| 6,495,659 | B2 | 12/2002 | Bentley et al. |
| 6,617,118 | B2 | 9/2003 | Roffler et al. |
| 6,737,505 | B2 | 5/2004 | Bentley et al. |
| 6,824,782 | B2 | 11/2004 | Whitlow et al. |
| 6,992,168 | B2 | 1/2006 | Bentley et al. |
| 7,012,135 | B2 | 3/2006 | Athwal et al. |
| 7,138,371 | B2 | 11/2006 | Defrees et al. |
| 7,205,380 | B2 | 4/2007 | Bentley et al. |
| 7,208,145 | B2 | 4/2007 | McManus et al. |
| 7,402,662 | B2 | 7/2008 | Athwal et al. |
| 7,416,858 | B2 | 8/2008 | Defrees |
| 7,446,174 | B2 | 11/2008 | Desjarlais et al. |
| 9,101,670 | B2 | 8/2015 | Bossard et al. |
| 9,636,412 | B2 * | 5/2017 | Bossard ............... C07K 16/241 |
| 2001/0026801 | A1 | 10/2001 | Tobinick |
| 2004/0121415 | A1 | 6/2004 | King et al. |
| 2004/0137557 | A1 | 7/2004 | Defrees et al. |
| 2005/0009988 | A1 | 1/2005 | Harris et al. |
| 2005/0074425 | A1 | 4/2005 | Waugh et al. |
| 2005/0180948 | A1 | 8/2005 | Desjarlais et al. |
| 2005/0271663 | A1 | 12/2005 | Ignatovich et al. |
| 2006/0073141 | A1 | 4/2006 | Ignatovich et al. |
| 2006/0177892 | A1 | 8/2006 | Defrees |
| 2006/0257360 | A1 | 11/2006 | Desjarlais et al. |
| 2006/0286066 | A1 | 12/2006 | Basran |
| 2007/0048219 | A1 | 3/2007 | Hsei et al. |
| 2007/0269369 | A1 | 11/2007 | Gegg et al. |
| 2010/0021481 | A1 | 1/2010 | Bossard et al. |
| 2016/0030587 | A1 | 2/2016 | Bossard et al. |

FOREIGN PATENT DOCUMENTS

| | | |
|---|---|---|
| GB | 2 246 570 A | 2/1992 |
| WO | WO 94/13322 | 6/1994 |
| WO | WO 96/34015 A1 | 10/1996 |
| WO | WO 98/25971 | 6/1998 |
| WO | WO 2001/94585 | 12/2001 |
| WO | WO 2003/099226 | 4/2003 |
| WO | WO 2003/080674 | 10/2003 |
| WO | WO 2004/074345 | 9/2004 |
| WO | WO 2004/081026 | 9/2004 |

(Continued)

OTHER PUBLICATIONS

Chapman, "PEGylated antibodies and antibody fragments for improved therapy: a review," Advanced Drug Delivery Reviews, 54, pp. 531-545, (2002).

Choy et al., "Efficacy of a novel PEGylated humanized anti-TNF fragment (CDP870) in patients with rheumatoid arthritis : a phase II double-blinded, randomized, dose-escalating trial," Rheumatology, vol. 41, pp. 1133-1137, (2002).

Co, et al., "Genetically Engineered Deglycosylation of the Variable Domain Increases the Affinity of an Anti-CD33 Monoclonal Antibody," Molecular Immunology, vol. 30, No. 15, pp. 1361-1367, (1993).

Edwards et al., "Design of PEGylated soluble tumor necrosis factor receptor type I (PEG sTNF-RI) for chronic inflammatory diseases," Advanced Drug Delivery Reviews, vol. 55, pp. 1315-1336, (2003).

(Continued)

*Primary Examiner* — Eric Olson

(74) *Attorney, Agent, or Firm* — Susan T. Evans

(57) ABSTRACT

Conjugates of an anti-TNF antibody and one or more nonpeptidic water-soluble polymers are provided. Typically, the nonpeptidic water-soluble polymer is poly(ethylene glycol) or a derivative thereof. Also provided, among other things, are compositions comprising conjugates, methods of making conjugates, and methods of administering compositions to a patient.

20 Claims, No Drawings

(56) References Cited

FOREIGN PATENT DOCUMENTS

WO WO 2005/105841 A2 11/2005
WO WO 2005/123778 A2 12/2005

OTHER PUBLICATIONS

Furst et al., "A Phase 2 Dose-finding Study of PEGylated Recombinant Methionyl Human Soluble Tumor Necrosis Factor Type I in Patients with Rheumatoid Arthritis," J. Rheumatology, vol. 32, pp. 2303-2310, (2005).
Kamada et al., "Antitumor Activity of Tumor Necrosis Factor-α Conjugated with Polyvinylpyrrolidone on Solid Tumors in Mice," Cancer Research, 60, pp. 6416-6420, (Nov. 15, 2000).
Kato, et al., "Activity enhancement of a lung cancer-associated human monoclonal antibody HB4C5 by N-deglycosylation," Hum. Antibod. Hybridomas, vol. 4, pp. 9-14, (1993).
Misseri et al., "TNF-α mediates obstruction-induced renal tubular cell apoptosis and proapoptotic signaling," Am. J. Physiol Renal Physiol, 288, pp. F406-F411, (2005).
Nash, et al., "Tumor necrosis factor inhibitors", MJA, vol. 183, No. 4, pp. 205-208, (2005).
Rose-John et al., "CDP-870 Celltech/Pfizer", Current Opinion Investigating Drugs, vol. 4, No. 5, pp. 588-592, (2003).
Sandborn, "Strategies for targeting tumour necrosis factor in IBD," Best Practice & Research Clinical Gastroenterology, vol. 17, No. 1, pp. 105-117 (2003).
Tsutsumi et al., "Site-specific chemical modification with polyethylene glycol of recombinant immunotoxin anti-Tac(Fv)-PE38 (LMB-2) improves antitumor activity and reduces animal toxicity and immunogenicity," PNAS, vol. 97, No. 15, pp. 8548-8553, (Jul. 18, 2000).
Tsutsumi et al., "In Vivo Anti-Tumor Efficacy of Polyethylene Glycol-modified Tumor Necrosis Factor-α Against Tumor Necrosis Factor-Resistant Tumors," Jpn. J. Cancer Res, vol. 87, pp. 1078-1085, (Oct. 1996).
Tsunoda et al., "Enhanced Antitumor Potency of Polyethylene Glycolylated Tumor Necrosis Factor-α: A Novel Polymer-Conjugation Technique with a Reversible Amino-Protective Reagent," The Journal of Pharmacology and Experimental Therapeutics, vol. 290, No. 1, pp. 368-372, (1999).
Wang et al., "Polyethylene Glycolated Recombinant TND Receptor I . . . ," Endocrinology, 143(9), pp. 3490-3497, (2002).
Worledge, et al., "Oral Administration of Avian Tumor Necrosis Factor Antibodies Effectively Treats Experimental Colitis in Rats", Digestive Diseases and Sciences, vol. 45, No. 12, pp. 2298-2305, (2000).
Yamamoto et al., "Site-specific PEGylation of a lysine-deficient TNF-α with full bioactivity," Nature Biotechnology, vol. 21, pp. 546-552, (2003).
Yang, et al., "Tailoring structure-function and pharmacokinetic properties of single-chain Fv proteins by site-specific PEGylation", Protein Engineering, vol. 16, No. 10, pp. 761-770, (2003).
International Search Report corresponding to PCT/US07/08738 dated Jul. 21, 2008.
Written Opinion of the International Search Report corresponding to PCT/US07/08738 dated Jul. 21, 2008.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).
Nektar™—Transforming Therapeutics, Nektar Advanced PEGylation: Polyethylene Glycol and Derivatives for Advanced PEGylation, 27 pages, Catalog—2004, (Jul. 2004).
NOF Corporation, PEG Derivatives, Phospholipid and Drug Delivery Materials for Pharmaceuticals, 46 pages, Catalogue 2003-1st, (Jan. 2003).
NOF Corporation, PEG Derivatives, Phospholipid and Drug Delivery Materials for Pharmaceuticals, 27 pages, Catalogue 2003-2nd, (Mar. 2004).
Polypure Products, PEG amines; PEG acids and amino acids; PEG thiols and disulfides; Biotins, 5 pages, (Apr. 2004).
Polypure Products, PEG amines; PEG acids and amino acids; PEG thiols and disulfides; Biotins, 5 pages, (Apr. 2005).
Quanta Biodesign, Labeling, Derivatization and Crosslinking Reagents for Biological and Related Materials with dPEG™, 38 pages, (Mar. 12, 2004).
Quanta Biodesign, Labeling, Modification and Crosslinking Reagents incorporating our unique monodispersed dPEG™ Technology, 31 pages, (Nov. 5, 2004).
Quanta Biodesign, Ltd., Leading innovator, producer and provider of monodisperse discrete PEG™ (dPEG™) derivatives, (Product Catalog), 26 pages, (Updated: Jul. 18, 2005).
Quanta Biodesign, Ltd., Leading innovator, producer and provider of monodisperse discrete PEG™ (dPEG™) derivatives, (Product Catalog), 26 pages, (Updated: Nov. 17, 2005).
Shearwater Polymers, Inc., Polyethylene Glycol Derivatives, 50 pages, Catalog—(Mar. 1995).
Shearwater Polymers, Inc., Polyethylene Glycol Derivatives, 55 pages, Catalog 1997-1998, (Jul. 1997).
Shearwater Polymers, Inc., Polyethylene Glycol and Derivatives: Functionalized Biocompatible Polymers for Research and Pharmaceuticals, 50 pages, Catalog—(Jan. 2000).
Shearwater Corporation, Polyethylene Glycol and Derivatives for Biomedical Applications, 20 pages, Catalog—(Jul. 2001).
Office Action corresponding to Canadian patent application No. 2,648,582 dated Jul. 8, 2013.
Canadian Office Action corresponding to Canadian Patent Application No. 2,648,582 dated Aug. 22, 2014.
Extended European Search Report corresponding to European patent application No. 07755116.6-1453 / 2004231 dated Jun. 12, 2013.
Office Action corresponding to Japanese patent application No. 2009-504347 dated May 28, 2012.
Office Action corresponding to Japanese patent application No. 2009-504347 dated Apr. 2, 2013.
Notice of Reasons for Rejection in Japanese Patent Application No. 2009-504347 dated Apr. 7, 2015.
Haug, et al., "A Phase I Trial of Immunosuppression with Anti-ICAM-1 (CD54) mAb in Renal Allograft Recipients", Transplantation, vol. 55, No. 4, pp. 766-773, (Apr. 1993).
Stephens, et al., "Comprehensive pharmacokinetics of a humanized antibody and analysis of residual anti-idiotypic responses", Immunology, vol. 85, pp. 668-674, (1995).
Canadian Office Communication corresponding to Canadian Patent Application No. 2,648,582 dated Sep. 23, 2015.
European Office Communication corresponding to European Patent Application No. 07 755 116.6 dated Jan. 30, 2017.
Japanese Notice of Reasons for Rejection corresponding to Japanese Patent Application No. 2009-504347 dated Feb. 12, 2016.
European Communication corresponding to European Patent Application No. 07 755 116.6-1109 dated Feb. 5, 2018.

* cited by examiner

CONJUGATES OF AN ANTI-TNF-ALPHA ANTIBODY

CROSS-REFERENCE TO RELATED APPLICATIONS

This application is a continuation of U.S. patent application Ser. No. 14/819,212, filed on Aug. 5, 2015, now U.S. Pat. No. 9,636,412, which is a continuation of U.S. patent application Ser. No. 12/296,268, filed on Sep. 22, 2009, now U.S. Pat. No. 9,101,670, which is a 35 USC § 371 application of International Application No. PCT/US2007/008738, filed Apr. 6, 2007, designating the United States, which claims the benefit of priority to U.S. Patent Application No. 60/790,339, filed Apr. 7, 2006, all of which are hereby incorporated by reference in their entireties.

FIELD

Among other things, one or more embodiments of the present invention relate generally to conjugates comprising an anti-TNFα antibody (e.g., an antibody having the ability to bind to tumor necrosis factor-alpha or "TNFα") and a polymer. In addition, the invention relates to (among other things) compositions comprising conjugates, methods for synthesizing conjugates, and methods of administering a composition.

BACKGROUND

Tumor necrosis factor-alpha ("TNFα), alternatively referred to as "cachexin" or "cachectin," is a 185 amino acid-long cytokine that is released by damaged white blood cells, endothelium cells and certain tissues. TNFα is formed in vivo by the cleavage of a 212 amino acid-long precursor transmembrane protein. Upon cleavage of this precursor transmembrane protein, soluble molecules are released that aggregate to form complexes. These complexes then bind to tumor necrosis factor receptors (TNF-R) found on a variety of cells to thereby result in an array of pro-inflammatory effects, such as the release of the pro-inflammatory cytokines interleukin-6 and interleukin-8, the enhancement of endothelial layer permeability (thereby allowing for leukocyte migration), the activation of neutrophils and eosinophils, and the induction of tissue-degrading enzymes produced by synoviocytes and chondrocytes.

Elevated levels of TNFα are associated with many disease states. For example, increased concentrations of TNFα are often found in the joints of individuals suffering from rheumatoid arthritis. In these patients, the induction of tissue-degrading enzymes by TNFα causes degradation and erosion of joint and bone tissues. In addition to rheumatoid arthritis, Crohn's disease is another disease associated with increased concentrations of TNFα. While the exact cause of Crohn's disease is unknown, patients suffering from Crohn's disease experience inflammation and ulceration of the digestive tract. Other diseases and conditions that have been linked to increased levels of TNFα include psoriatic arthritis, ulcerative colitis, plaque psoriasis, sarcoidosis, ankylosis spondylitis, and cytokine-induced islet destruction in autoimmune diabetes.

Current approaches for treating individuals suffering from rheumatoid arthritis (as well as other diseases associated with increased TNFα) include neutralizing or otherwise diminishing the ability of TNFα to bind to TNFα receptors in the body. In one such approach, patients are administered monoclonal antibodies that bind to TNFα (i.e., anti-TNFα- antibodies), thereby inhibiting TNFα's ability to bind to TNFα receptors. Commercially available forms of anti-TNFα-antibodies are available, including, infliximab (marketed under the REMICADE® name, Centocor, Inc., Malvern, Pa.) and adalimumab (marketed under the HUMIRA™ name, Abbott Laboratories, Abbott Park, Ill.). Infliximab is typically administered over at least two hours via an intravenous infusion while adalimumab is typically administered subcutaneously every two weeks. Because infliximab is a chimeric antibody, there is concern that administration of this antibody to humans can result in an immunogenic reaction. Further, even though adalimumab is a human monoclonal antibody specific for TNF, approximately 5% of adult rheumatoid arthritis patients developed low-titer antibodies to adalimumab at least once during treatment (as demonstrated over three studies) and the long term immunogenicity of adalimumab is unknown.

Another approach for neutralizing or diminishing the effects of TNFα includes binding circulating TNFα, thereby reducing the amount of TNFα available for binding to functioning cell surface receptors. This approach can be effected by administering TNFα receptors (or TNFα-like receptors). By administering an excess of exogenous TNFα receptors (or TNFα-like receptors), circulating TNFα is bound to the exogenous and non-functioning receptors resulting in significantly decreased amounts of TNFα available for activating endogenous TNFα receptors. Commercially available pharmaceutical formulations that are based on this approach include etanercept (marketed under the ENBREL®, Immunex Corporation, Thousand Oaks, Calif.), a p75 type II TNF soluble receptor. Although not currently available commercially, PEGsunercept (or PEG-sTNF-RI) is a PEGylated version of a p55 type I TNF receptor. It has been alleged that etanercept has been associated with rare cases of central nervous system disorders such as multiple sclerosis, myelitis and optic neuritis and pancytopenia, including aplastic anemia. There is relatively little experience with PEGsunercept to know whether it will suffer from the same concerns as etanercept.

Thus, there remains a need to address, for example, the immunogenicity concerns associated with therapies intended to decrease the effects TNFα in vivo. The present invention is intended to address the immunogenicity concerns (and/or other concerns) by, for example, attaching a water-soluble polymer to an anti-TNF antibody, thereby forming a conjugate between the water-soluble polymer and the anti-TNF antibody. The present invention includes this and other embodiments, which are believed to be new and completely unsuggested by the art.

SUMMARY

Accordingly, a conjugate is provided, the conjugate comprising an anti-TNFα antibody covalently attached, either directly or through a spacer moiety, to a nonpeptidic water-soluble polymer. The conjugate is typically provided as part of a composition.

In one or more embodiments of the invention, a conjugate is provided, the conjugate comprising a residue of an anti-TNFα antibody covalently attached through a hydrolytically stable linkage to a water-soluble polymer.

In one or more embodiments of the invention, a conjugate is provided, the conjugate comprising a residue of an anti-TNFα antibody covalently attached to a water-soluble polymer.

In one or more embodiments of the invention, a conjugate is provided, the conjugate comprising a residue of an anti- TNFα antibody covalently attached to a water-soluble polymer, wherein the anti-TNFα antibody is covalently attached at an amine.

In one or more embodiments of the invention, a conjugate is provided, the conjugate comprising a residue of an anti-TNFα antibody covalently attached to a linear water-soluble polymer.

In one or more embodiments of the invention, a conjugate is provided, the conjugate comprising a residue of an anti-TNFα antibody covalently attached to a branched water-soluble polymer.

In one or more embodiments of the invention, the anti-TNFα antibody used to form the conjugate is not a dimer or trimer (and therefore the corresponding anti-TNFα antibody residue within the conjugate is not a dimer or trimer).

In one or more embodiments of the invention, the anti-TNFα antibody used to form the conjugate is monovalent (and therefore the corresponding anti-TNFα antibody residue within the conjugate is monovalent).

In one or more embodiments of the invention, the anti-TNFα antibody used to form the conjugate is not a CDR-grafted (and therefore the corresponding anti-TNFα antibody residue within the conjugate is not CDR-grafted).

In one or more embodiments of the invention, the anti-TNFα antibody used to form the conjugate is a full length antibody (and therefore the corresponding anti-TNFα antibody residue within the conjugate is a full length antibody).

In one or more embodiments of the invention, the anti-TNFα antibody used to form the conjugate is not galactosylated (and therefore the corresponding anti-TNFα antibody residue within the conjugate is not a galactosylated).

In one or more embodiments of the invention, the anti-TNFα antibody used to form the conjugate is not glycosylated (and therefore the corresponding anti-TNFα antibody residue within the conjugate is not glycosylated).

In one or more embodiments of the invention, a conjugate is provided, the conjugate comprising the following structure:

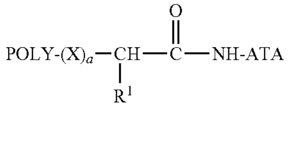

wherein:

POLY is a water-soluble polymer;

(a) is either zero or one;

X, when present, is a spacer moiety comprised of one or more atoms;

$R^1$ is H or an organic radical containing 1 to 3 carbon atoms; and

ATA is a residue of an anti-TNFα antibody.

In one or more embodiments of the invention, a conjugate is provided, the conjugate comprising the following structure:

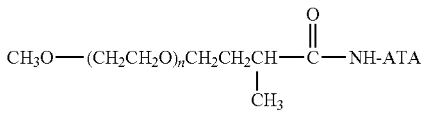

wherein n ranges from about 3 to about 1400 and ATA is a residue of an anti-TNFα antibody.

In one or more embodiments of the invention, a conjugate is provided, the conjugate comprising the following structure:

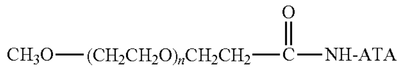

wherein n ranges from about 3 to about 1400 and ATA is a residue of an anti-TNFα antibody.

In one or more embodiments of the invention, a conjugate is provided, the conjugate comprising the following structure:

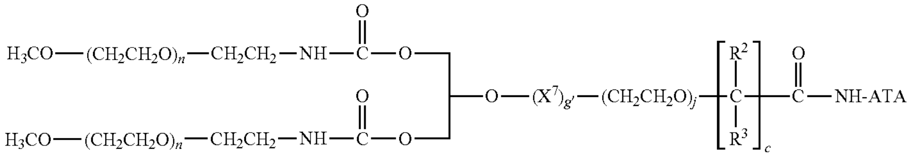

wherein:

(n) is 2 to 4000;

(g') is 0, 1, 2 or 3;

(c) is 1 to 10;

each $R^2$ is H or an organic radical;

each $R^3$ is H or an organic radical;

(j) is 0 to 20; and

ATA is a residue of an anti-TNFα antibody.

In one or more embodiments of the invention, a conjugate is provided, the conjugate comprising the following structure:

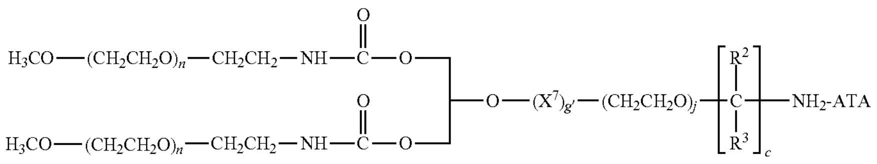

wherein:

(n) is 2 to 4000;

(g') is 0, 1, 2 or 3;

(c) is 1 to 10;

each $R^2$ is H or an organic radical;

each $R^3$ is H or an organic radical;

(j) is 0 to 20; and

ATA is a residue of an anti-TNFα antibody.

In one or more embodiments of the invention, a conjugate is provided, the conjugate comprising the following structure:

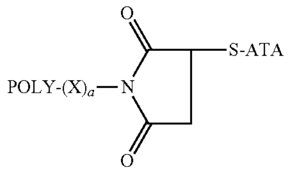

wherein:

POLY is a water-soluble polymer;

(a) is either zero or one;

X, when present, is a spacer moiety comprised of one or more atoms; and

ATA is a residue of an anti-TNFα antibody.

In one or more embodiments of the invention, a conjugate is provided, the conjugate comprising the following structure:

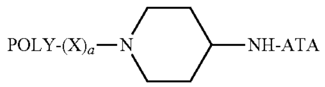

wherein:

POLY is a water-soluble polymer;

(a) is either zero or one;

X, when present, is a spacer moiety; and

ATA is a residue of an anti-TNFα antibody.

In one or more embodiments of the invention, a conjugate is provided, the conjugate comprising the following structure:

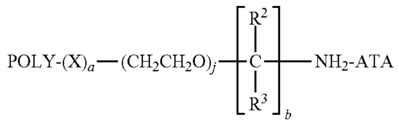

wherein:

POLY is a water-soluble polymer;

(a) is either zero or one;

(j) is zero or an integer from 1 to about 20;

(b) is zero or an integer from 1 to about 10;

each $R^2$, when present, is H or an organic radical;

each $R^3$, when present, Is H or an organic radical; and

ATA is a residue of an anti-TNFα antibody.

In one or more embodiments of the invention, the water-soluble polymer used to form the conjugate is poly(ethylene glycol). The weight average molecular weight of the water-soluble polymer can be within one or more of the following ranges: from about 6,000 Daltons to about 100,000 Daltons; from about 10,000 Daltons to about 85,000 Daltons; and from about 20,000 Daltons to about 65,000 Daltons.

In one or more embodiments of the invention, the anti-TNFα antibody used to form the conjugate is either infliximab or adalimumab (and therefore the corresponding anti-TNFα antibody residue located with the conjugate is either infliximab or adalimumab).

In one or more embodiments of the invention, a composition is provided, the composition comprising a plurality of conjugates, each conjugate comprised of a residue of an anti-TNF antibody attached, either directly or through a spacer moiety comprised of one or more atoms, to a PEG molecule, wherein at least 50% of all conjugates in the composition are N-terminally monoPEGylated.

In one or more embodiments of the invention, a composition is provided, the composition comprising a plurality of conjugates, each conjugate comprised of a residue of an anti-TNF antibody attached, either directly or through a spacer moiety comprised of one or more atoms, to a water-soluble polymer, wherein at least 75% of all conjugates in the composition have a residue of an anti-TNF antibody attached, either directly or through a spacer moiety comprised of one or more atoms, to five or fewer water-soluble polymers.

In one or more embodiments of the invention, a composition is provided, the composition comprising a plurality of conjugates, each conjugate comprised of a residue of an anti-TNF antibody attached, either directly or through a spacer moiety comprised of one or more atoms, to a water-soluble polymer, wherein at least 75% of all conjugates in the composition have a residue of an anti-TNF antibody attached, either directly or through a spacer moiety comprised of one or more atoms, to three or fewer water-soluble polymers.

In one or more embodiments of the invention, a method for delivering a conjugate is provided, the method comprising the step of subcutaneously administering to the patient a composition comprised of a conjugate of a residue of an anti-TNF antibody and a water-soluble polymer.

DETAILED DESCRIPTION

Before describing one or more embodiments of the present invention in detail, it is to be understood that this invention is not limited to the particular polymers, synthetic techniques, anti-TNF antibodies, and the like, as such may vary.

It must be noted that, as used in this specification and the intended claims, the singular forms "a," "an," and "the" include plural referents unless the context clearly dictates otherwise. Thus, for example, reference to "a polymer" includes a single polymer as well as two or more of the same or different polymers, reference to "an optional excipient" refers to a single optional excipient as well as two or more of the same or different optional excipients, and the like.

In describing and claiming one or more embodiments of the present invention, the following terminology will be used in accordance with the definitions described below.

"PEG," "polyethylene glycol" and "poly(ethylene glycol)" as used herein, are interchangeable and encompass any nonpeptidic water-soluble poly(ethylene oxide). Typically, PEGs for use in accordance with the invention comprise the following structure "$-(OCH_2CH_2)_n-$" where (n) is 2 to 4000. As used herein, PEG also includes "$-CH_2CH_2-O(CH_2CH_2O)_n-CH_2CH_2-$" and "$-(OCH_2CH_2)_nO-$," depending upon whether or not the terminal oxygens have been displaced. Throughout the specification and claims, it should be remembered that the term "PEG" includes structures having various terminal or "end capping" groups and so forth. The term "PEG" also means a polymer that contains a majority, that is to say, greater than 50%, of —$OCH_2CH_2$— repeating subunits. With respect to specific forms, the PEG can take any number of a variety of molecular weights, as well as structures or geometries such as "branched," "linear," "forked," "multifunctional," and the like, to be described in greater detail below.

The terms "end-capped" and "terminally capped" are interchangeably used herein to refer to a terminal or end-point of a polymer having an end-capping moiety. Typically, although not necessarily, the end-capping moiety comprises a hydroxy or $C_{1-20}$ alkoxy group, more preferably a $C_{1-10}$ alkoxy group, and still more preferably a $C_{1-5}$ alkoxy group. Thus, examples of end-capping moieties include alkoxy (e.g., methoxy, ethoxy and benzyloxy), as well as aryl, heteroaryl, cyclo, heterocyclo, and the like. It must be remembered that the end-capping moiety may include one or more atoms of the terminal monomer in the polymer [e.g., the end-capping moiety "methoxy" in $CH_3O(CH_2CH_2O)_n$— and $CH_3(OCH_2CH_2)_n$—]. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, and the like. Suitable detectors include photometers, films, spectrometers, and the like. The end-capping group can also advantageously comprise a phospholipid. When the polymer has an end-capping group comprising a phospholipid, unique properties are imparted to the polymer and the resulting conjugate. Exemplary phospholipids include, without limitation, those selected from the class of phospholipids called phosphatidylcholines. Specific phospholipids include, without limitation, those selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

"Non-naturally occurring" with respect to a polymer as described herein, means a polymer that in its entirety is not found in nature. A non-naturally occurring polymer of the invention may, however, contain one or more monomers or segments of monomers that are naturally occurring, so long as the overall polymer structure is not found in nature.

The term "water soluble" as in a "water-soluble polymer" is any polymer that is soluble in water at room temperature. Typically, a water-soluble polymer will transmit at least about 75%, more preferably at least about 95%, of light transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer is about 95% (by weight) soluble in water or completely soluble in water.

Molecular weight in the context of a water-soluble polymer, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight or the use of light scattering techniques, ultracentrifugation or viscometry to determine weight average molecular weight. The polymers of the invention are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

The term "active" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "non-reactive" or "inert" group).

As used herein, the term "functional group" or any synonym thereof is meant to encompass protected forms thereof as well as unprotected forms.

The terms "spacer moiety," "linkage" and "linker" are used herein to refer to an atom or a collection of atoms optionally used to link interconnecting moieties such as a terminus of a polymer segment and an anti-TNF antibody or an electrophile or nucleophile of an anti-TNF antibody. The spacer moiety may be hydrolytically stable or may include a physiologically hydrolyzable or enzymatically degradable linkage. Unless the context clearly dictates otherwise, a spacer moiety optionally exists between any two elements of a compound (e.g., the provided conjugates comprising a residue of the anti-TNF antibody and water-soluble polymer can attached directly or indirectly through a spacer moiety).

"Alkyl" refers to a hydrocarbon chain, typically ranging from about 1 to 15 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl as well as cycloalkylene-containing alkyl.

"Lower alkyl" refers to an alkyl group containing from 1 to 6 carbon atoms, and may be straight chain or branched, as exemplified by methyl, ethyl, n-butyl, i-butyl, and t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8 carbon atoms. "Cycloalkylene" refers to a cycloalkyl group that is inserted into an alkyl chain by bonding of the chain at any two carbons in the cyclic ring system.

"Alkoxy" refers to an —O—R group, wherein R is alkyl or substituted alkyl, preferably $C_{1-6}$ alkyl (e.g., methoxy, ethoxy, propyloxy, and so forth).

The term "substituted" as in, for example, "substituted alkyl," refers to a moiety (e.g., an alkyl group) substituted with one or more noninterfering substituents, such as, but not limited to: alkyl, $C_{3-8}$ cycloalkyl, e.g., cyclopropyl, cyclobutyl, and the like; halo, e.g., fluoro, chloro, bromo, and iodo; cyano; alkoxy, lower phenyl; substituted phenyl; and the like. "Substituted aryl" is aryl having one or more noninterfering groups as a substituent. For substitutions on a phenyl ring, the substituents may be in any orientation (i.e., ortho, meta, or para).

"Noninterfering substituents" are those groups that, when present in a molecule, are typically nonreactive with other functional groups contained within the molecule.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably sulfur, oxygen, or nitrogen, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom that is not a carbon. Preferred heteroatoms include sulfur, oxygen, and nitrogen.

"Substituted heteroaryl" is heteroaryl having one or more noninterfering groups as substituents.

"Substituted heterocycle" is a heterocycle having one or more side chains formed from noninterfering substituents.

An "organic radical" as used herein shall include alkyl, substituted alkyl, aryl, substituted aryl.

"Electrophile" and "electrophilic group" refer to an ion or atom or collection of atoms, that may be ionic, having an electrophilic center, i.e., a center that is electron seeking, capable of reacting with a nucleophile.

"Nucleophile" and "nucleophilic group" refers to an ion or atom or collection of atoms that may be ionic having a nucleophilic center, i.e., a center that is seeking an electrophilic center or with an electrophile.

A "physiologically cleavable" or "hydrolyzable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include, but are not limited to, the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Pharmaceutically acceptable excipient" or "carrier" refers to an excipient that may optionally be included in the compositions of the invention and that causes no significant adverse toxicological effects to the patient. "Pharmacologically effective amount," "physiologically effective amount," and "therapeutically effective amount" are used interchangeably herein to mean the amount of a polymer-anti-TNF antibody conjugate that is needed to provide a desired level of the conjugate (or corresponding unconjugated anti-TNF antibody) in the bloodstream or in the target tissue. The precise amount will depend upon numerous factors, e.g., the particular anti-TNF antibody, the components and physical characteristics of the therapeutic composition, intended patient population, individual patient considerations, and the like, and can readily be determined by one skilled in the art, based upon the information provided herein.

"Multi-functional" means a polymer having three or more functional groups contained therein, where the functional groups may be the same or different. Multi-functional polymeric reagents of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer backbone.

The term "anti-TNFα antibody" as used herein, refers to an a moiety (such as a full length antibody) which neutralizes the biological activity of human TNFα through binding to human TNFα, thereby decreasing the ability of the bound human TNFα bind to anti-TNFα receptors. The anti-TNFα antibody will also have at least one electrophilic group or nucleophilic group suitable for reaction with a polymeric reagent. In addition, the term "anti-TNFα antibody" encompasses both the anti-TNFα antibody prior to conjugation as well as the anti-TNFα antibody residue following conjugation. As will be explained in further detail below, one of ordinary skill in the art can determine whether any given moiety is an anti-TNFα antibody. Exemplary anti-TNFα antibodies include infliximab and adalimumab.

The term "substantially homologous" means that a particular subject sequence, for example, a mutant sequence, varies from a reference sequence by one or more substitutions, deletions, or additions, the net effect of which does not result in an adverse functional dissimilarity between the reference and subject sequences. For purposes of the present invention, sequences having greater than 95 percent homology, equivalent biological properties, and equivalent expression characteristics are considered substantially homologous. For purposes of determining homology, truncation of the mature sequence should be disregarded. Sequences having lesser degrees of homology, comparable bioactivity, and equivalent expression characteristics are considered substantial equivalents.

The term "fragment" means any fragment of a full length anti-TNFα antibody that retains the ability to bind to TNFα.

The term "patient," refers to a living organism suffering from or prone to a condition that can be prevented or treated by administration of an active agent (e.g., conjugate), and includes both humans and animals.

"Optional" or "optionally" means that the subsequently described circumstance may or may not occur, so that the description includes instances where the circumstance occurs and instances where it does not.

"Substantially" means nearly totally or completely, for instance, satisfying one or more of the following: greater than 50%, 51% or greater, 75% or greater, 80% or greater, 90% or greater, and 95% or greater of the condition.

Amino acid residues in peptides are abbreviated as follows: Phenylalanine is Phe or F; Leucine is Leu or L;

Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G.

Unless the context clearly dictates otherwise, when the term "about" precedes a numerical value, the numerical value is understood to mean±10% of the stated numerical value.

Turning to one or more embodiments of the invention, a conjugate is provided, the conjugate comprising an anti-TNFα antibody covalently attached, either directly or through a spacer moiety, to a nonpeptidic water-soluble polymer. The conjugates of the invention will have one or more of the following features.

The Anti-TNFα Antibody

As previously stated, the conjugate generically comprises an anti-TNFα antibody covalently attached, either directly or through a spacer moiety, to a nonpeptidic water-soluble polymer. As used herein, the term "anti-TNFα antibody" shall refer to the anti-TNFα antibody prior to conjugation as well as to the anti-TNFα antibody following attachment to a nonpeptidic water-soluble polymer. It will be understood, however, that when the original anti-TNFα antibody is attached to a nonpeptidic water-soluble polymer, the anti-TNFα antibody is slightly altered due to the presence of one or more covalent bonds associated with linkage to the polymer optionally through a spacer moiety. Often, this slightly altered form of the anti-TNFα antibody attached to another molecule is referred to a "residue" of the anti-TNFα antibody. The anti-TNFα antibody in the conjugate can be any peptide that provides anti-TNFα antibody activity.

The anti-TNFα antibody can be derived from conventional techniques for forming antibodies.

For any given antibody proposed to be an anti-TNFα antibody suitable for use in the conjugates described herein, it is possible to determine whether that moiety has anti-TNFα antibody activity. For example, it is possible to adhere a composition comprising the proposed antibody to column and pass labeled human TNFα through the column. Subsequent detection of labels being retained on the column (as the result of having been bound to the proposed antibody) indicates that the proposed antibody is suitable for use as an anti-TNFα antibody herein.

The Water-Soluble Polymer

As previously discussed, each conjugate comprises an anti-TNFα antibody attached to a water-soluble polymer. With respect to the water-soluble polymer, the water-soluble polymer is nonpeptidic, nontoxic, non-naturally occurring and biocompatible. With respect to biocompatibility, a substance is considered biocompatible if the beneficial effects associated with use of the substance alone or with another substance (e.g., an active agent such as an anti-TNF antibody) in connection with living tissues (e.g., administration to a patient) outweighs any deleterious effects as evaluated by a clinician, e.g., a physician. With respect to non-immunogenicity, a substance is considered nonimmunogenic if the intended use of the substance in vivo does not produce an undesired immune response (e.g., the formation of antibodies) or, if an immune response is produced, that such a response is not deemed clinically significant or important as evaluated by a clinician. It is particularly preferred that the nonpeptidic water-soluble polymer is biocompatible and nonimmunogenic.

Further, the polymer is typically characterized as having from 2 to about 300 termini. Examples of such polymers include, but are not limited to, poly(alkylene glycols) such as polyethylene glycol ("PEG"), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), and combinations of any of the foregoing.

The polymer is not limited to a particular structure and can be linear (e.g., alkoxy PEG or bifunctional PEG), branched or multi-armed (e.g., forked PEG or PEG attached to a polyol core), dendritic, or with degradable linkages. Moreover, the internal structure of the polymer can be organized in any number of different patterns and can be selected from the group consisting of homopolymer, alternating copolymer, random copolymer, block copolymer, alternating tripolymer, random tripolymer, and block tripolymer.

Typically, activated PEG and other activated water-soluble polymers (i.e., polymeric reagents) are activated with a suitable activating group appropriate for coupling to a desired site on the anti-TNF antibody. Thus, a polymeric reagent will possess a reactive group for reaction with the anti-TNF antibody. Representative polymeric reagents and methods for conjugating these polymers to an active moiety are known in the art and further described in Zalipsky, S., et al., "*Use of Functionalized Poly(Ethylene Glycols) for Modification of Polypeptides*" in Polyethylene Glycol Chemistry: Biotechnical and Biomedical Applications, J. M. Harris, Plenus Press, New York (1992), and in Zalipsky (1995) *Advanced Drug Reviews* 16:157-182.

Typically, the weight-average molecular weight of the water-soluble polymer in the conjugate is from about 100 Daltons to about 150,000 Daltons. Exemplary ranges, however, include weight-average molecular weights in the range of greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 85,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, and in the range of from about 40,000 Daltons to about 120,000 Daltons. For any given water-soluble polymer, PEGs having a molecular weight in one or more of these ranges are preferred.

Exemplary weight-average molecular weights for the water-soluble polymer include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble polymer (e.g., a branched 40,000 Dalton water-soluble polymer comprised of two 20,000 Dalton polymers) having a total molecular weight of any of the foregoing can also be used. In one or more embodiments, the conjugate will not have any PEG moieties attached, either directly or indirectly, with a PEG having a weight average molecular weight of less than about 6,000 Daltons.

When used as the polymer, PEGs will typically comprise a number of $(OCH_2CH_2)$ monomers [or $(CH_2CH_2O)$ monomers, depending on how the PEG is defined]. As used throughout the description, the number of repeating units is identified by the subscript "n" in "$(OCH_2CH_2)_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

One particularly preferred polymer for use in the invention is an end-capped polymer, that is, a polymer having at least one terminus capped with a relatively inert group, such as a lower $C_{1-6}$ alkoxy group, although a hydroxyl group can also be used. When the polymer is PEG, for example, it is preferred to use a methoxy-PEG (commonly referred to as mPEG), which is a linear form of PEG wherein one terminus of the polymer is a methoxy ($—OCH_3$) group, while the other terminus is a hydroxyl or other functional group that can be optionally chemically modified.

In one form useful in one or more embodiments of the present invention, free or unbound PEG is a linear polymer terminated at each end with hydroxyl groups:

$$HO—CH_2CH_2O—(CH_2CH_2O)_n—CH_2CH_2—OH,$$

wherein (n) typically ranges from zero to about 4,000.

The above polymer, alpha-, omega-dihydroxylpoly(ethylene glycol), can be represented in brief form as HO-PEG-OH where it is understood that the -PEG- symbol can represent the following structural unit:

$$—CH_2CH_2O—(CH_2CH_2O)_n—CH_2CH_2—,$$

wherein (n) is as defined as above.

Another type of PEG useful in one or more embodiments of the present invention is methoxy-PEG-OH, or mPEG in brief, in which one terminus is the relatively inert methoxy group, while the other terminus is a hydroxyl group. The structure of mPEG is given below.

$$CH_3O—CH_2CH_2O—(CH_2CH_2O)_n—CH_2CH_2—OH$$

wherein (n) is as described above.

Multi-armed or branched PEG molecules, such as those described in U.S. Pat. No. 5,932,462, can also be used as the PEG polymer. For example, PEG can have the structure:

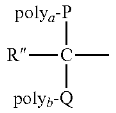

wherein:

$poly_a$ and $poly_b$ are PEG backbones (either the same or different), such as methoxy poly(ethylene glycol);

R" is a nonreactive moiety, such as H, methyl or a PEG backbone; and

P and Q are nonreactive linkages. In a preferred embodiment, the branched PEG polymer is methoxy poly(ethylene glycol) disubstituted lysine. Depending on the specific anti-TNF antibody used, the reactive ester functional group of the disubstituted lysine may be further modified to form a functional group suitable for reaction with the target group within the anti-TNF antibody.

In addition, the PEG can comprise a forked PEG. An example of a forked PEG is represented by the following structure:

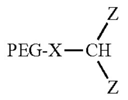

wherein: X is a spacer moiety of one or more atoms and each Z is an activated terminal group linked to CH by a chain of atoms of defined length. International Application No. PCT/US99/05333, discloses various forked PEG structures capable of use in one or more embodiments of the present invention. The chain of atoms linking the Z functional groups to the branching carbon atom serve as a tethering group and may comprise, for example, alkyl chains, ether chains, ester chains, amide chains and combinations thereof.

The PEG polymer may comprise a pendant PEG molecule having reactive groups, such as carboxyl, covalently attached along the length of the PEG rather than at the end of the PEG chain. The pendant reactive groups can be attached to the PEG directly or through a spacer moiety, such as an alkylene group.

In addition to the above-described forms of PEG, the polymer can also be prepared with one or more weak or degradable linkages in the polymer, including any of the above-described polymers. For example, PEG can be prepared with ester linkages in the polymer that are subject to hydrolysis. As shown below, this hydrolysis results in cleavage of the polymer into fragments of lower molecular weight:

$$\text{-PEG-}CO_2\text{—PEG-}+H_2O \longrightarrow \text{-PEG-}CO_2H\text{+HO-PEG-}$$

Other hydrolytically degradable linkages, useful as a degradable linkage within a polymer backbone, include: carbonate linkages; imine linkages resulting, for example, from reaction of an amine and an aldehyde (see, e.g., Ouchi et al. (1997) *Polymer Preprints* 38(1):582-3); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; orthoester linkages that are, for example, formed by reaction between a formate and an alcohol; amide linkages formed by an amine group, e.g., at an end of a polymer such as PEG, and a carboxyl group of another PEG chain; urethane linkages formed from reaction of, e.g., a PEG with a terminal isocyanate group and a PEG alcohol; peptide linkages formed by an amine group, e.g., at an end of a polymer such as PEG, and a carboxyl group of a peptide; and oligonucleotide linkages formed by, for example, a phosphoramidite group, e.g., at the end of a polymer, and a 5' hydroxyl group of an oligonucleotide.

Such optional features of the conjugate, i.e., the introduction of one or more degradable linkages into the polymer chain, may provide for additional control over the final desired pharmacological properties of the conjugate upon administration. For example, a large and relatively inert conjugate (i.e., having one or more high molecular weight PEG chains attached thereto, for example, one or more PEG chains having a molecular weight greater than about 10,000, wherein the conjugate possesses essentially no bioactivity) may be administered, which is hydrolyzed to generate a bioactive conjugate possessing a portion of the original PEG chain. In this way, the properties of the conjugate can be more effectively tailored to balance the bioactivity of the conjugate over time.

The water-soluble polymer associated with the conjugate can also be "cleavable." That is, the water-soluble polymer cleaves (either through hydrolysis, enzymatic processes, or otherwise), thereby resulting in the unconjugated anti-TNF antibody. In some instances, cleavable polymers detach from the anti-TNF antibody in vivo without leaving any fragment of the water-soluble polymer. In other instances, cleavable polymers detach from the anti-TNF antibody in vivo leaving a relatively small fragment (e.g., a succinate tag) from the water-soluble polymer. An exemplary cleavable polymer includes one that attaches to the anti-TNF antibody via a carbonate linkage.

Those of ordinary skill in the art will recognize that the foregoing discussion concerning nonpeptidic and water-soluble polymer is by no means exhaustive and is merely illustrative, and that all polymeric materials having the qualities described above are contemplated. As used herein, the term "polymeric reagent" generally refers to an entire molecule, which can comprise a water-soluble polymer segment and a functional group.

As described above, a conjugate of the invention comprises a water-soluble polymer covalently attached to an anti-TNFα antibody. Typically, for any given conjugate, there will be one to three water-soluble polymers covalently attached to one or more moieties having anti-TNF antibody activity. In some instances, however, the conjugate may have 1, 2, 3, 4, 5, 6, 7, 8 or more water-soluble polymers individually attached to an anti-TNFα antibody.

The particular linkage within the anti-TNFα antibody and the polymer depends on a number of factors. Such factors include, for example, the particular linkage chemistry employed, the particular anti-TNFα antibody, the available functional groups within the anti-TNFα antibody (either for attachment to a polymer or conversion to a suitable attachment site), the presence of additional reactive functional groups within the anti-TNFα antibody, and the like.

Typically, a hydrolytically stable linkage, such as an amide, urethane (also known as carbamate), amine, thioether (also known as sulfide), or urea (also known as carbamide) linkage is employed as the linkage for coupling the anti-TNFα antibody. Again, a preferred hydrolytically stable linkage is an amide. In one approach, a water-soluble polymer bearing an activated ester can be reacted with an amine group on the anti-TNFα antibody to thereby result in an amide linkage.

For conjugates possessing a hydrolytically stable linkage that couples the anti-TNFα antibody to the polymer, the conjugate will typically possess a measurable degree of bioactivity. For instance, such conjugates are typically characterized as having a bioactivity satisfying one or more of the following percentages relative to that of the unconjugated anti-TNF antibody: at least about 2%, at least about 5%, at least about 10%, at least about 15%, at least about 25%, at least about 30%, at least about 40%, at least about 50%, at least about 60%, at least about 80%, at least about 85%, at least about 90%, at least about 95%, at least about 97%, at least about 100%, and more than 105% (when measured in a suitable model, such as those well known in the art). Preferably, conjugates having a hydrolytically stable linkage (e.g., an amide linkage) will possess at least some degree of the bioactivity of the unmodified parent anti-TNFα antibody.

Amino groups on anti-TNFα antibody provide a point of attachment between the anti-TNFα antibody and the water-soluble polymer. Lysine residues, each having an ε-amino acid that may be available for conjugation. Further, the N-terminal amine of anti-TNFα antibody can also serve as a point of attachment.

There are a number of examples of suitable polymeric reagents useful for forming covalent linkages with available amines of an anti-TNFα antibody. Specific examples, along with the corresponding conjugate, are provided in Table 1, below. In the table, the variable (n) represents the number of repeating monomeric units and "—NH-ATA" represents the residue of the anti-TNFα antibody following conjugation to the polymeric reagent. While each polymeric portion [e.g., $(OCH_2CH_2)_n$ or $(CH_2CH_2O)_n$] presented in Table 1 terminates in a "$CH_3$" group, other groups (such as H and benzyl) can be substituted therefor.

TABLE 1

| Amine-Specific Polymeric Reagents and the anti-TNFα antibody Conjugate Formed Therefrom | |
|---|---|
| Polymeric Reagent | Corresponding Conjugate |
| 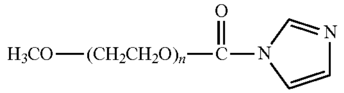<br>mPEG-Oxycarbonylimidazole Derivative | 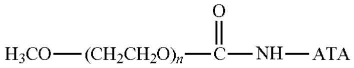<br>Carbamate Linkage |
| 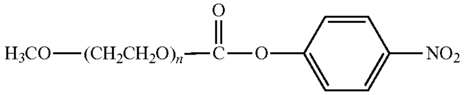<br>mPEG Nitrophenyl Derivative | 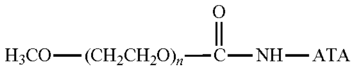<br>Carbamate Linkage |
| 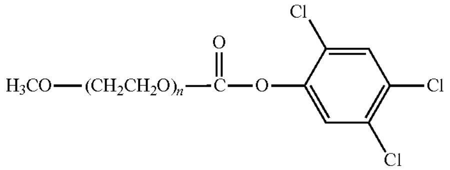<br>mPEG-Trichlorophenyl Carbonates | 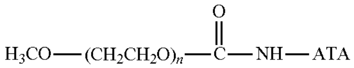<br>Carbamate Linkage |
| 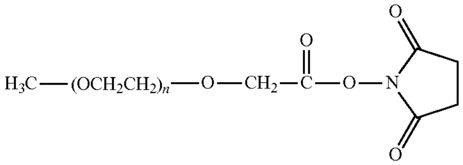<br>mPEG-Succinimidyl Derivative | 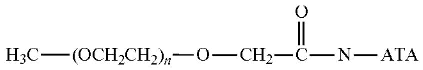<br>Amide Linkage |
| 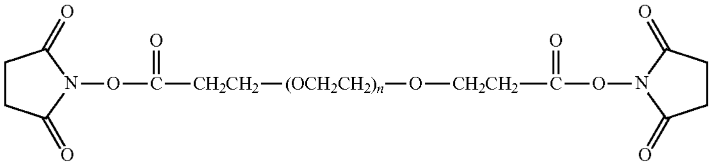<br>Homobifunctional PEG-Succinimidyl Derivative | 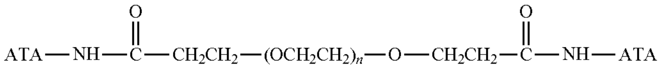<br>Amide Linkages |

TABLE 1-continued

| Amine-Specific Polymeric Reagents and the anti-TNFα antibody Conjugate Formed Therefrom | |
|---|---|
| Polymeric Reagent | Corresponding Conjugate |
| 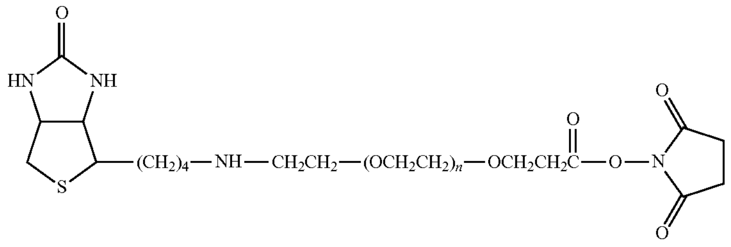<br>Heterobifunctional PEG-Succinimidyl Derivative | 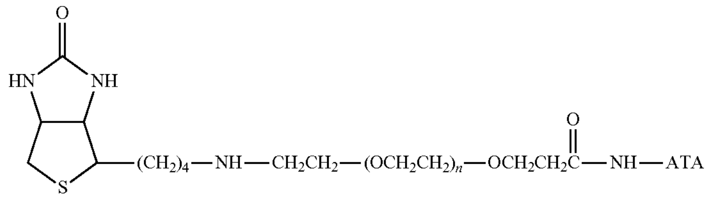<br>Amide Linkage |
| 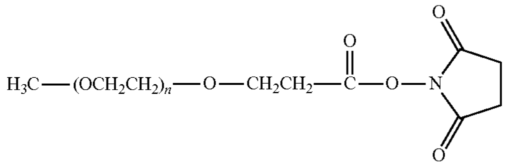<br>mPEG-Succinimidyl Derivative | 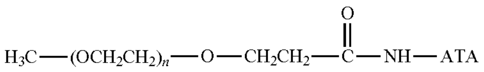<br>Amide Linkage |
| 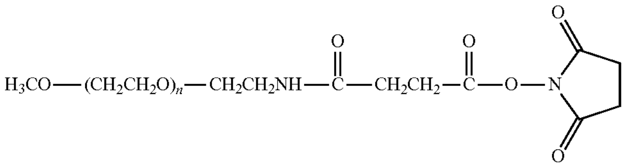<br>mPEG-Succinimdyl Derivative | 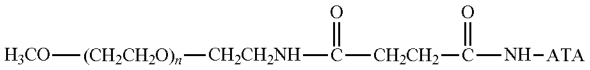<br>Amide Linkage |
| 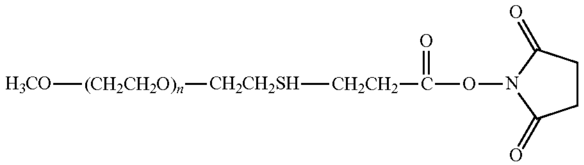<br>mPEG Succinimidyl Derivative | 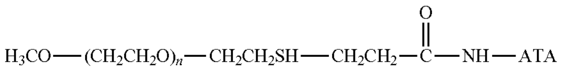<br>Amide Linkage |

TABLE 1-continued
Amine-Specific Polymeric Reagents and the anti-TNFα antibody Conjugate Formed Therefrom
| Polymeric Reagent | Corresponding Conjugate |
|---|---|
| 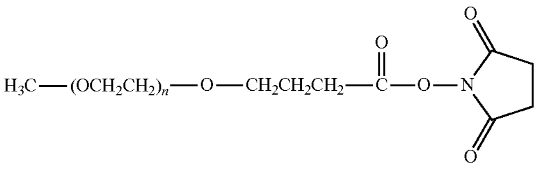 mPEG-Succinimidyl Derivative | 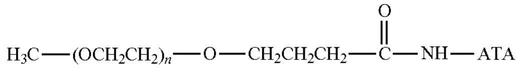 Amide Linkage |
| 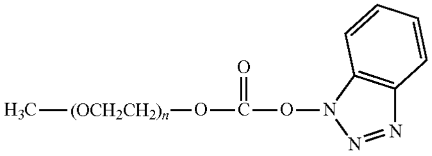 mPEG-Benzotriazole Carbonate Derivative | 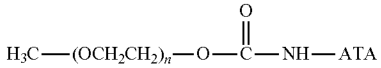 Carbamate Linkage |
| 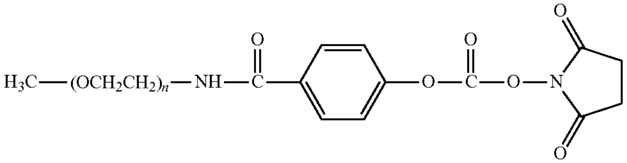 mPEG-Succinimidyl Derivative | 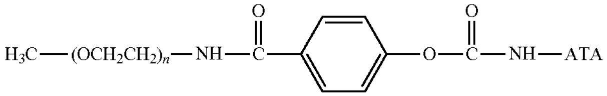 Carbamate Linkage |
| 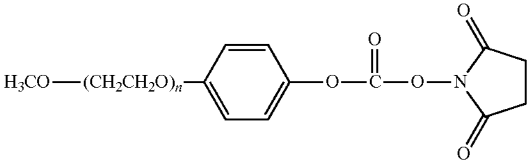 mPEG-Succinimidyl Derivative | 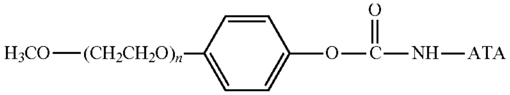 Amide Linkage |

TABLE 1-continued

| Amine-Specific Polymeric Reagents and the anti-TNFα antibody Conjugate Formed Therefrom | |
|---|---|
| Polymeric Reagent | Corresponding Conjugate |
| 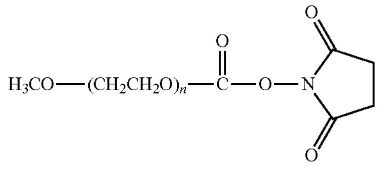 mPEG Succinimidyl Derivative | 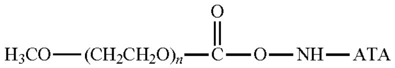 Amide Linkage |
| 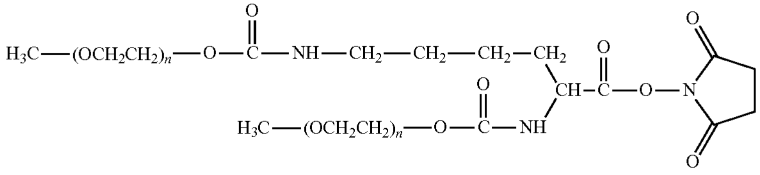 Branched mPEG2-N-Hydroxysuccinimide Derivative | 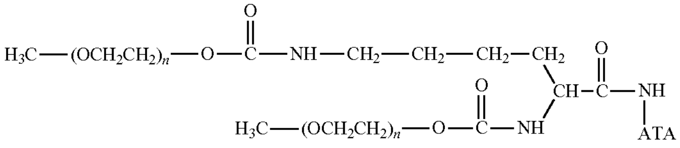 Amide Linkage |
| 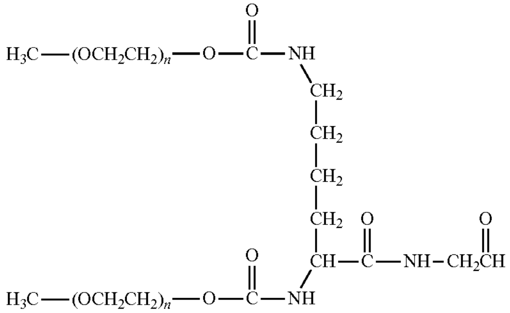 Branched mPEG2-Aldehyde Derivative | 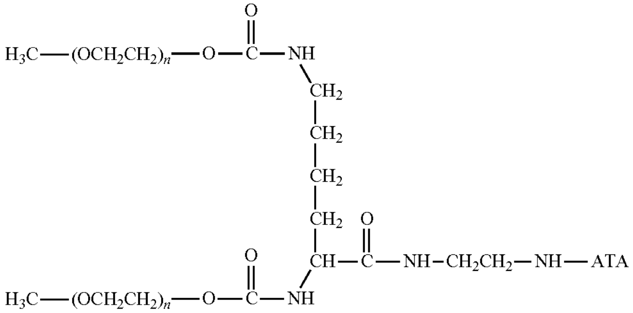 Secondary Amine Linkage |
| 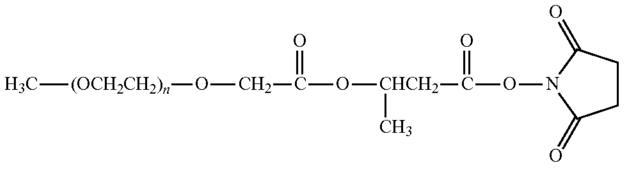 mPEG-Succinimidyl Derivative | 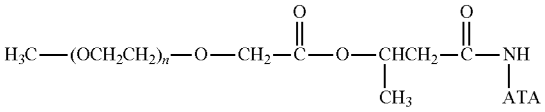 Amide Linkage |

TABLE 1-continued

| Amine-Specific Polymeric Reagents and the anti-TNFα antibody Conjugate Formed Therefrom | |
|---|---|
| Polymeric Reagent | Corresponding Conjugate |
| 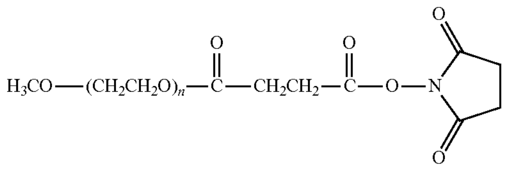 mPEG-Succinimidyl Derivative | 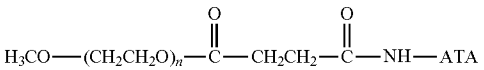 Amide Linkage |
| 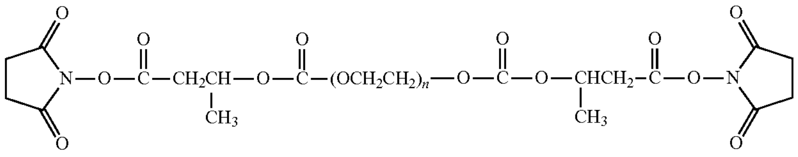 Homobifunctional PEG-Succinimidyl Derivative | 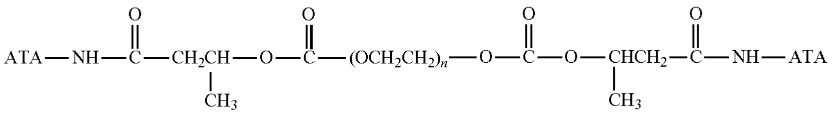 Amide Linkages |
| 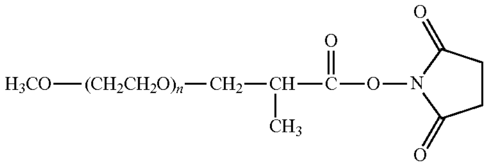 mPEG-Succinimidyl Derivative | 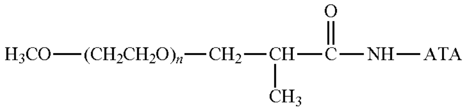 Amide Linkage |
| 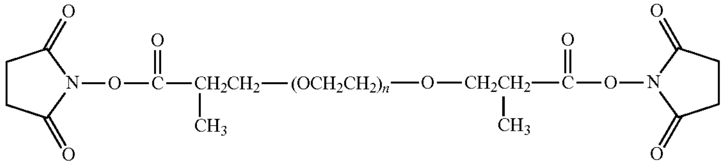 Homobifunctional PEG-Succinimidyl Propionate Derivative | 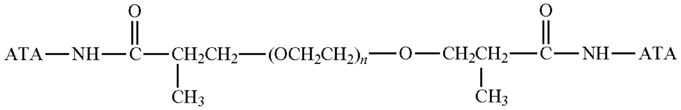 Amide Linkages |

TABLE 1-continued

| Amine-Specific Polymeric Reagents and the anti-TNFα antibody Conjugate Formed Therefrom | |
|---|---|
| Polymeric Reagent | Corresponding Conjugate |
| 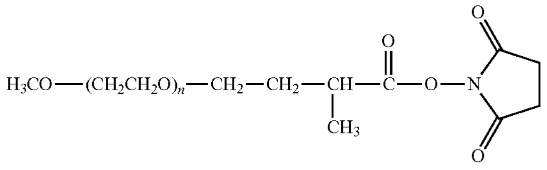 mPEG-Succinimidyl Derivative | 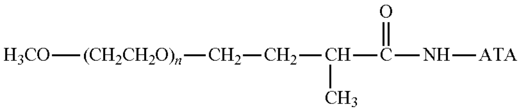 Amide Linkage |
| 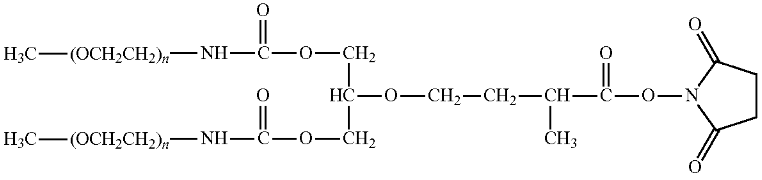 Branched mPEG2-N-Hydroxysuccinimide Derivative | 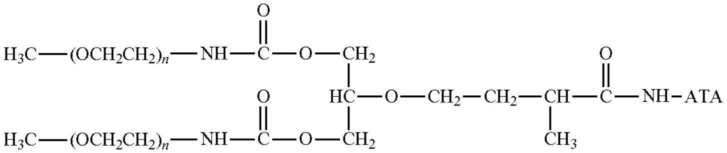 Amide Linkage |
| 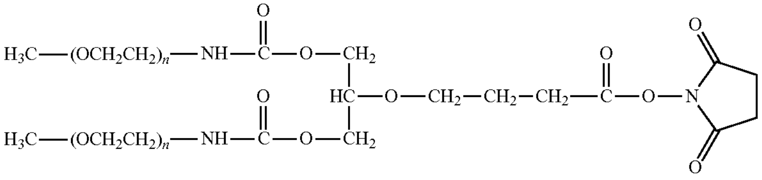 Branched mPEG2-N-Hydroxysuccinimide Derivative | 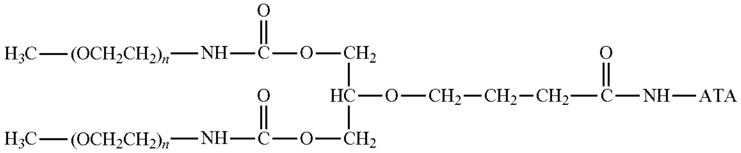 Amide Linkage |
| 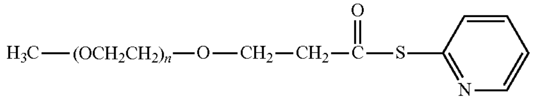 mPEG-Thioester Derivative | 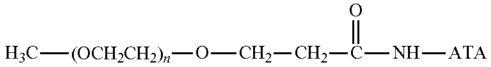 Amide Linkage (typically to anti-TNFα antibody having an N-terminal cysteine or histidine) |
| 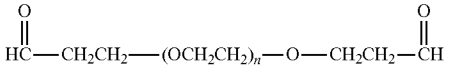 Homobifunctional PEG Propionaldehyde Derivative | 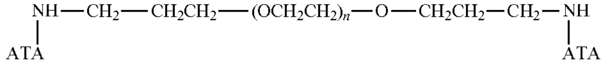 Secondary Amine Linkages |

TABLE 1-continued

Amine-Specific Polymeric Reagents and the anti-TNFα antibody Conjugate Formed Therefrom

| Polymeric Reagent | Corresponding Conjugate |
| --- | --- |
| 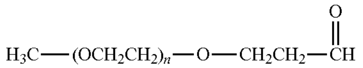 mPEG Propionaldehyde Derivative | $H_3C—(OCH_2CH_2)_n—O—CH_2CH_2—CH_2—NH—ATA$ Secondary Amine Linkage |
| 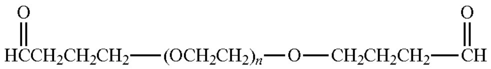 Homobifunctional PEG Butyraldehyde Derivative | 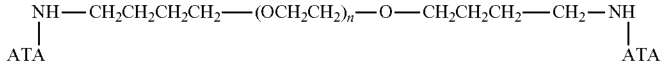 Secondary Amine Linkages |
| 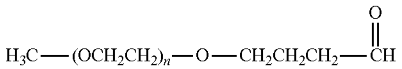 mPEG Butryaldehyde Derivative | $H_3C—(OCH_2CH_2)_n—O—CH_2CH_2CH_2—CH_2—NH—ATA$ Secondary Amine Linkage |
| 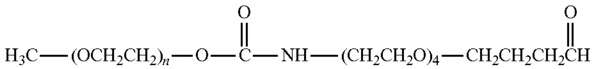 mPEG Butryaldehyde Derivative | 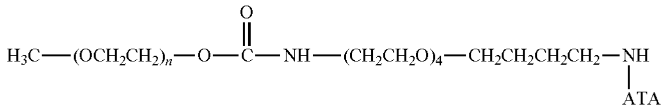 Secondary Amine Linkage |
| 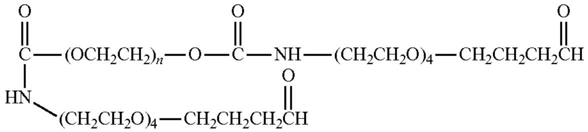 Homobifunctional PEG Butryaldehyde Derivative | 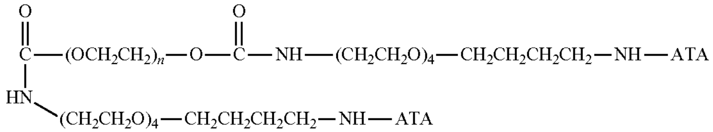 Secondary Amine Linkages |
| 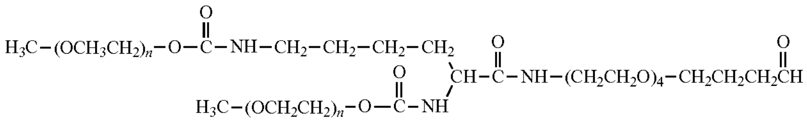 Branched mPEG2 Butyraldehyde Derivative | 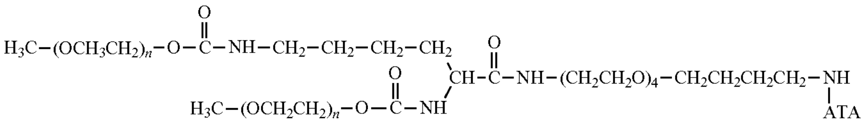 Secondary Amine Linkage |

TABLE 1-continued

| Amine-Specific Polymeric Reagents and the anti-TNFα antibody Conjugate Formed Therefrom | |
|---|---|
| Polymeric Reagent | Corresponding Conjugate |
| 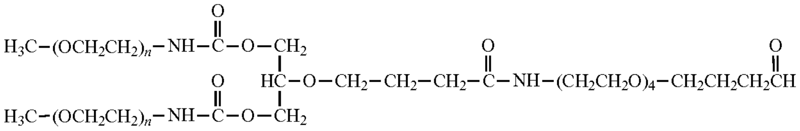<br>Branched mPEG2 Butyraldehyde Derivative | 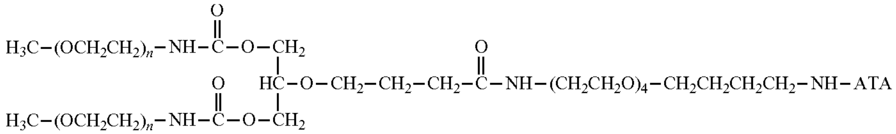<br>Secondary Amine Linkage |
| 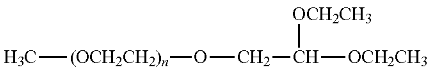<br>mPEG Acetal Derivative | $H_3C—(OCH_2CH_2)_n—O—CH_2CH_2—NH—ATA$<br>Secondary Amine Linkage |
| 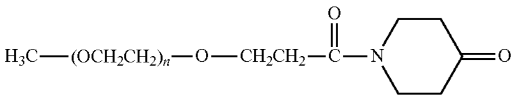<br>mPEG Piperidone Derivative | 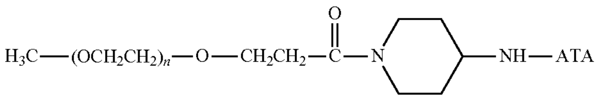<br>Secondary Amine Linkage (to a secondary carbon) |
| 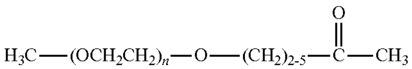<br>mPEG Methylketone Derivative | 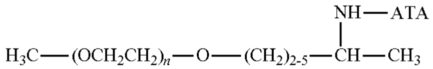<br>secondary amine linkage (to a secondary carbon) |
| 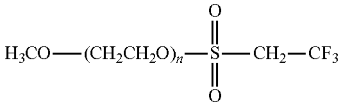<br>mPEG tresylate | $H_3CO—(CH_2CH_2O)_n—CH_2CH_2—NH—ATA$<br>Secondary Amine Linkage |

TABLE 1-continued

| Amine-Specific Polymeric Reagents and the anti-TNFα antibody Conjugate Formed Therefrom | |
|---|---|
| Polymeric Reagent | Corresponding Conjugate |
| 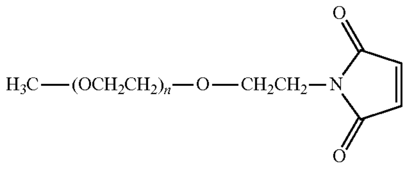 mPEG Maleimide Derivative (under certain reaction conditions such as pH > 8) | 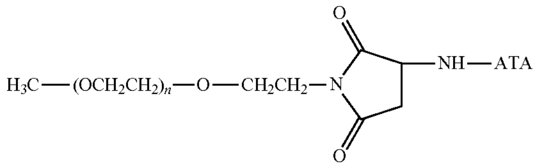 Secondary Amine Linkage |
| 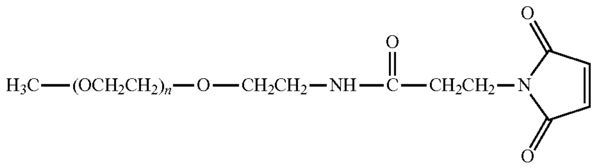 mPEG Maleimide Derivative (under certain reaction conditions such as pH > 8) | 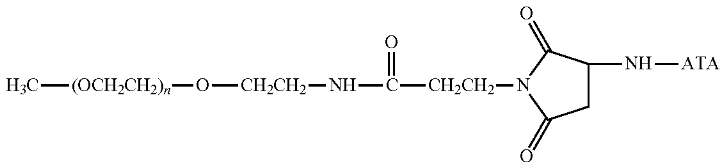 Secondary Amine Linkage |
| 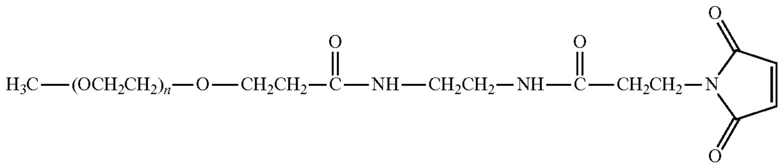 mPEG Maleimide Derivative (under certain reaction conditions such as pH > 8) | 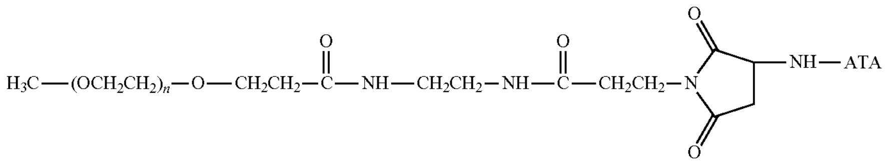 Secondary Amine Linkage |

TABLE 1-continued

| Amine-Specific Polymeric Reagents and the anti-TNFα antibody Conjugate Formed Therefrom | |
|---|---|
| Polymeric Reagent | Corresponding Conjugate |
| 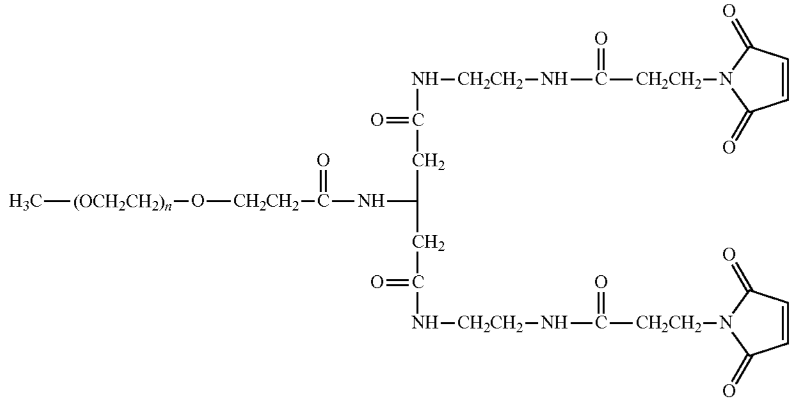 mPEG Forked Maleimide Derivative (under certain reaction conditions such as pH > 8) | 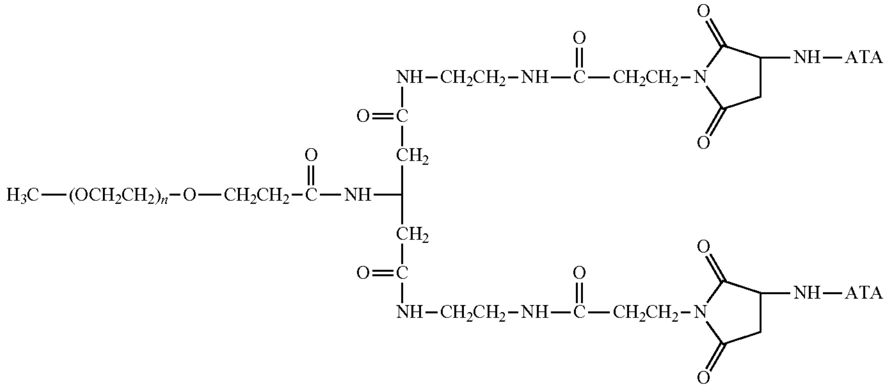 Secondary Amine Linkages |
| 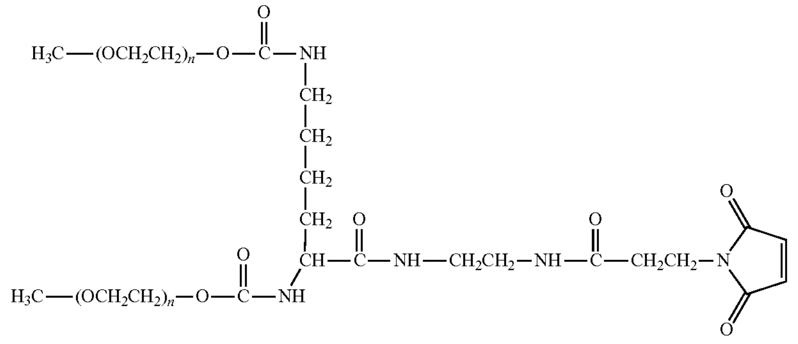 branched mPEG2 Maleimide Derivative (under certain reaction conditions such as pH > 8) | 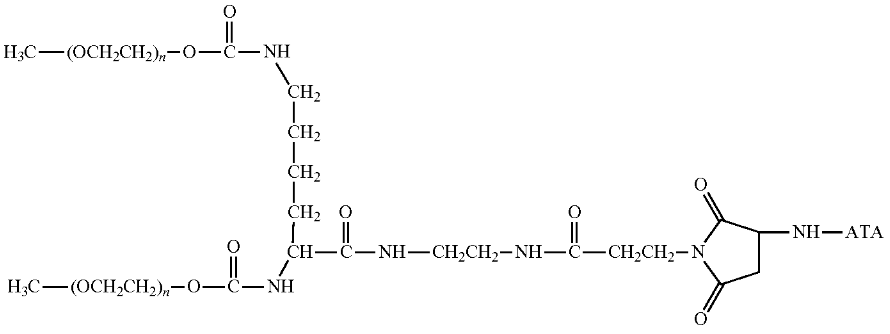 Secondary Amine Linkage |

Conjugation of a polymeric reagent to an amino group of an anti-TNFα antibody can be accomplished by a variety of techniques. In one approach, an anti-TNFα antibody can be conjugated to a polymeric reagent functionalized with a succinimidyl derivative (or other activated ester group, wherein approaches similar to those described for these alternative activated ester group-containing polymeric reagents can be used). In this approach, the polymer bearing a succinimidyl derivative can be attached to the anti-TNFα antibody in an aqueous media at a pH of 7 to 9.0, although using different reaction conditions (e.g., a lower pH such as 6 to 7, or different temperatures and/or less than 15° C.) can result in the attachment of the polymer to a different location on the anti-TNFα antibody. In addition, an amide linkage can be formed reacting an amine-terminated nonpeptidic, water-soluble polymer with an anti-TNFα antibody bearing an activating a carboxylic acid group.

Typical of another approach useful for conjugating the anti-TNFα antibody to a polymeric reagent is use of reductive amination to conjugate a primary amine of an anti-TNFα antibody with a polymeric reagent functionalized with a ketone, aldehyde or a hydrated form thereof (e.g., ketone hydrate, aldehyde hydrate). In this approach, the primary amine from the anti-TNFα antibody reacts with the carbonyl group of the aldehyde or ketone (or the corresponding hydroxyl-containing group of a hydrated aldehyde or ketone), thereby forming a Schiff base. The Schiff base, in turn, can then be reductively converted to a stable conjugate through use of a reducing agent such as sodium borohydride. Selective reactions (e.g., at the N-terminus are possible) are possible, particularly with a polymer functionalized with a ketone or an alpha-methyl branched aldehyde and/or under specific reaction conditions (e.g., reduced pH).

Carboxyl groups represent another functional group that can serve as a point of attachment on the anti-TNF antibody. Structurally, the conjugate will comprise the following:

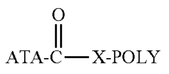

where ATA and the adjacent carbonyl group corresponds to the carboxyl-containing anti-TNFα antibody, X is a linkage, preferably a heteroatom selected from O, N(H), and S, and POLY is a water-soluble polymer such as PEG, optionally terminating in an end-capping moiety.

The C(O)—X linkage results from the reaction between a polymeric derivative bearing a terminal functional group and a carboxyl-containing anti-TNFα antibody. As discussed above, the specific linkage will depend on the type of functional group utilized. If the polymer is end-functionalized or "activated" with a hydroxyl group, the resulting linkage will be a carboxylic acid ester and X will be O. If the polymer backbone is functionalized with a thiol group, the resulting linkage will be a thioester and X will be S. When certain multi-arm, branched or forked polymers are employed, the C(O)X moiety, and in particular the X moiety, may be relatively more complex and may include a longer linkage structure.

Water-soluble derivatives containing a hydrazide moiety are also useful for conjugation at a carbonyl. To the extent that the anti-TNFα antibody moiety does not contain a carbonyl moiety, a carbonyl moiety can be introduced by reducing any carboxylic acids (e.g., the C-terminal carboxylic acid) and/or by providing glycosylated or glycated (wherein the added sugars have a carbonyl moiety) versions of the anti-TNFα antibody. Specific examples of water-soluble derivatives containing a hydrazide moiety, along with the corresponding conjugates, are provided in Table 2, below. In addition, any water-soluble derivative containing an activated ester (e.g., a succinimidyl group) can be converted to contain a hydrazide moiety by reacting the water-soluble polymer derivative containing the activated ester with hydrazine ($NH_2$—$NH_2$) or tert-butyl carbazate [$NH_2NHCO_2C(CH_3)_3$]. In the table, the variable (n) represents the number of repeating monomeric units and "═C-ATA" represents the residue of the anti-TNFα antibody following conjugation to the polymeric reagent. Optionally, the hydrazone linkage can be reduced using a suitable reducing agent. While each polymeric portion [e.g., $(OCH_2CH_2)_n$ or $(CH_2CH_2O)_n$] presented in Table 2 terminates in a "$CH_3$" group, other groups (such as H and benzyl) can be substituted therefor.

TABLE 2

Carboxyl-Specific Polymeric Reagents and the anti-TNFα antibody Conjugate Formed Therefrom

| Polymeric Reagent | Corresponding Conjugate |
|---|---|
| 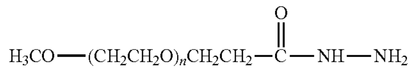 | 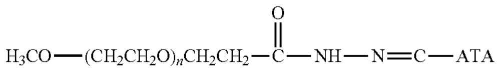 |
| mPEG-Hydrazine Derivative | Hydrazone Linkage |
| 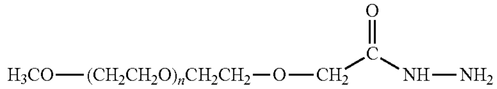 | 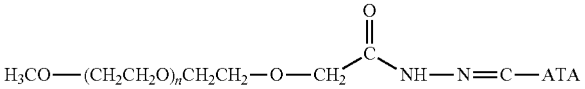 |
| mPEG-Hydrazine Derivative | Hydrazone Linkage |
| 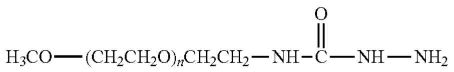 | 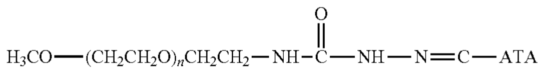 |
| mPEG-Hydrazine Derivative | Hydrazone Linkage |
| 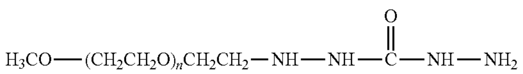 | 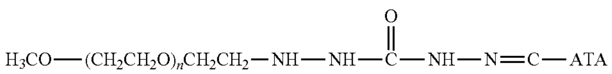 |

TABLE 2-continued

| Carboxyl-Specific Polymeric Reagents and the anti-TNFα antibody Conjugate Formed Therefrom | |
|---|---|
| Polymeric Reagent | Corresponding Conjugate |
| mPEG-Hydrazine Derivative | Hydrazone Linkage |
| 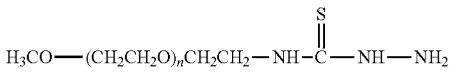 | 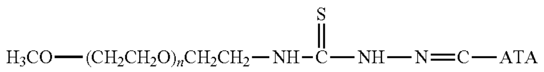 |
| mPEG-Hydrazine Derivative | Hydrazone Linkage |
| 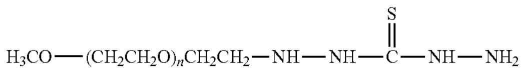 | 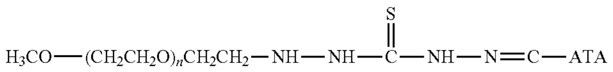 |
| mPEG-Hydrazine Derivative | Hydrazone Linkage |
| 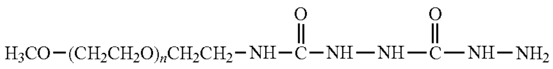 | 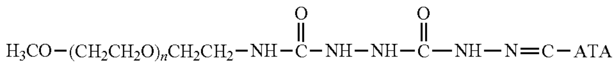 |
| mPEG-Hydrazine Derivative | Hydrazone Linkage |
| 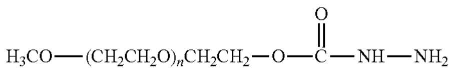 | 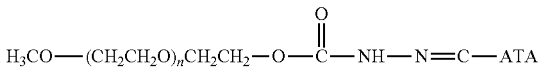 |
| mPEG-Hydrazine Derivative | Hydrazone Linkage |

Thiol groups contained within the anti-TNFα antibody can serve as effective sites of attachment for the water-soluble polymer. In particular, cysteine residues provide thiol groups when the anti-TNFα antibody contains a cysteine. The thiol groups in such cysteine residues can then be reacted with an activated PEG that is specific for reaction with thiol groups, e.g., an N-maleimidyl polymer or other derivative, as described in U.S. Pat. No. 5,739,208 and in International Patent Publication No. WO 01/62827.

Specific examples, along with the corresponding conjugate, are provided in Table 3, below. In the table, the variable (n) represents the number of repeating monomeric units and "—S-ATA" represents the anti-TNFα antibody residue following conjugation to the water-soluble polymer. While each polymeric portion [e.g., $(OCH_2CH_2)_n$ or $(CH_2CH_2O)_n$] presented in Table 3 terminates in a "$CH_3$" group, other groups (such as H and benzyl) can be substituted therefor.

TABLE 3

| Thiol-Specific Polymeric Reagents and the anti-TNFα antibody Conjugate Formed Therefrom | |
|---|---|
| Polymeric Reagent | Corresponding Conjugate |
| 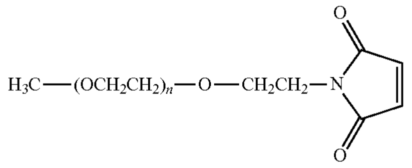<br>mPEG Maleimide Derivative | 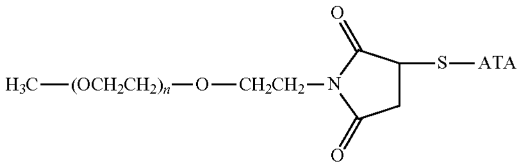<br>Thioether Linkage |
| 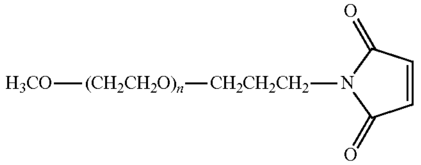<br>mPEG Maleimide Derivative | 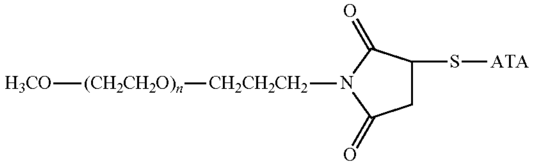<br>Thioether Linkage |
| 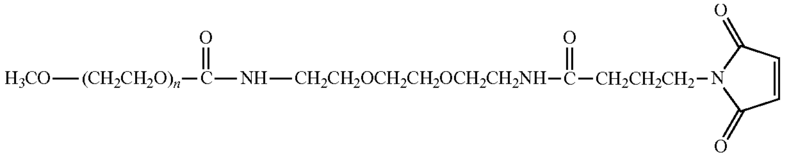<br>mPEG Maleimide Derivative | 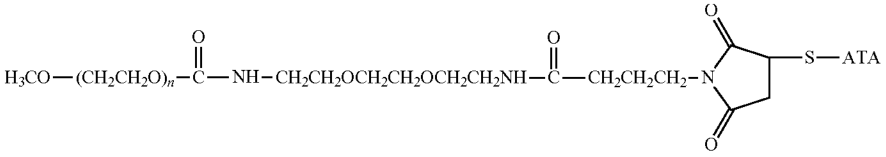<br>Thioether Linkage |
| 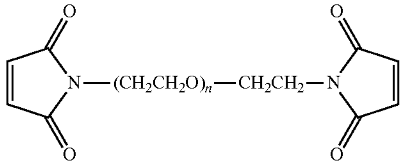<br>Homobifunctional mPEG Maleimide Derivative | 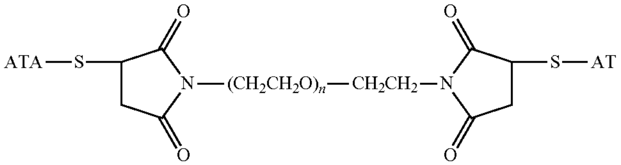<br>Thioether Linkages |

TABLE 3-continued
| Thiol-Specific Polymeric Reagents and the anti-TNFα antibody Conjugate Formed Therefrom | |
|---|---|
| Polymeric Reagent | Corresponding Conjugate |
| 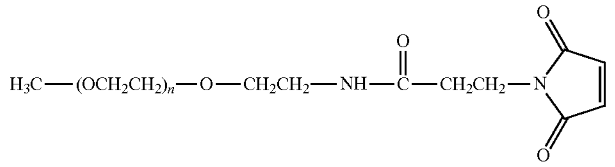 mPEG Maleimide Derivative | 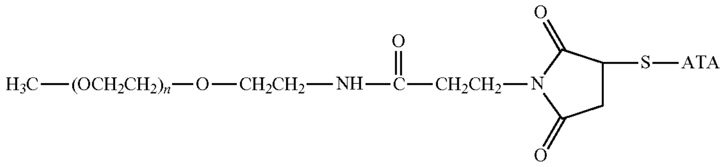 Thioether Linkage |
| 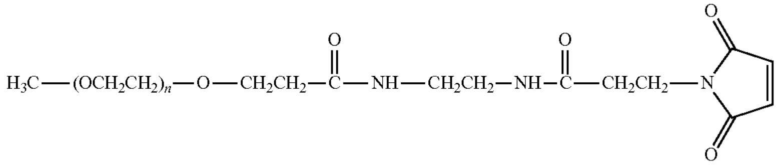 mPEG Maleimide Derivative | 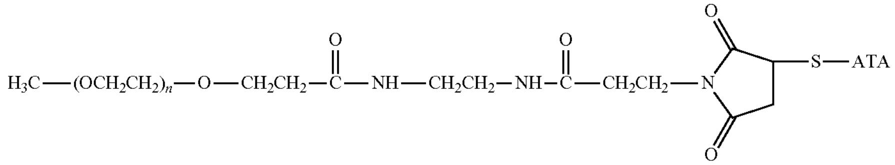 Thioether Linkage |
| 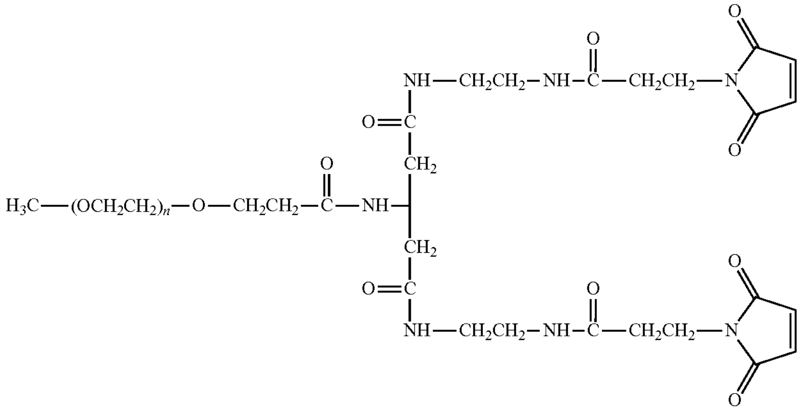 mPEG Forked Maleimide Derivative | 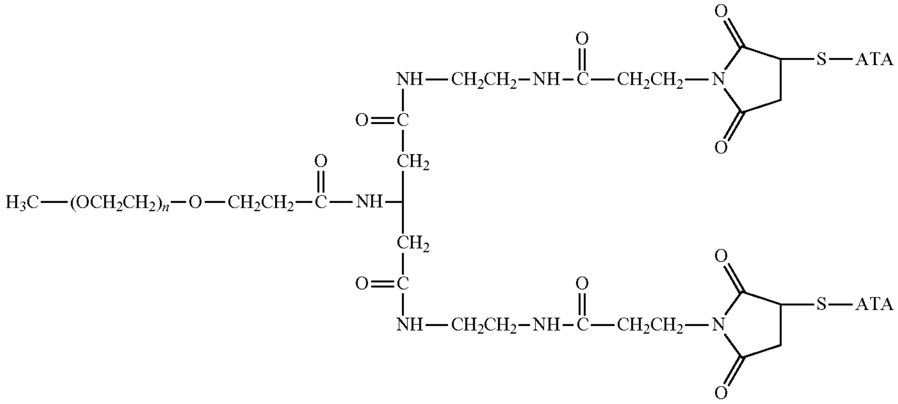 Thioether Linkage |

TABLE 3-continued
| Thiol-Specific Polymeric Reagents and the anti-TNFα antibody Conjugate Formed Therefrom | |
|---|---|
| Polymeric Reagent | Corresponding Conjugate |
| 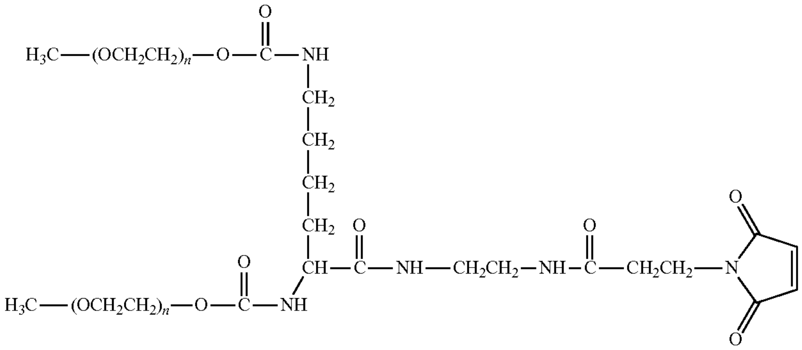 branched mPEG2 Maleimide Derivative | 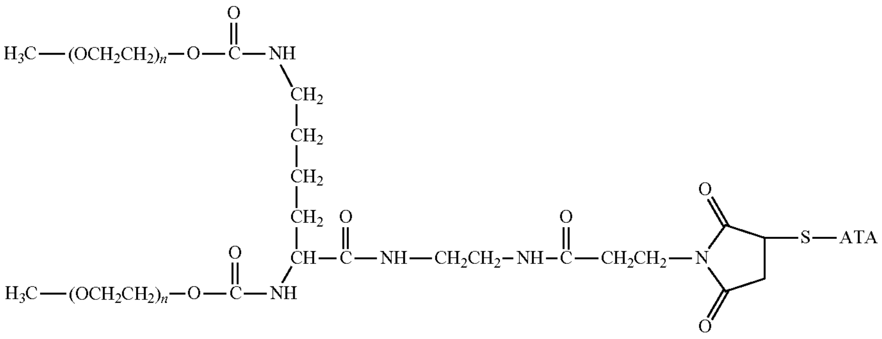 Thioether Linkage |
| 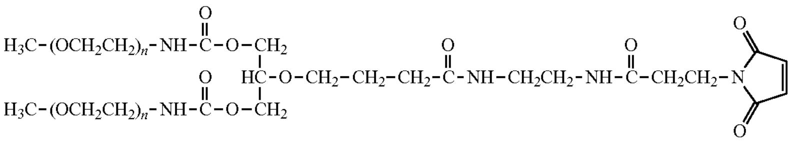 branched mPEG2 Maleimide Derivative | 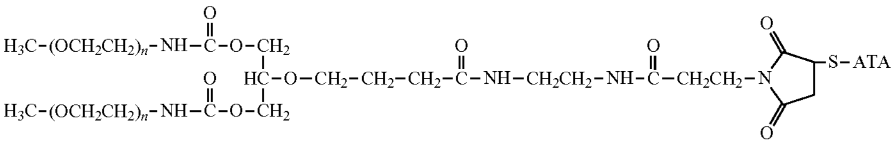 Thioether Linkage |

TABLE 3-continued
Thiol-Specific Polymeric Reagents and the anti-TNFα antibody Conjugate Formed Therefrom
| Polymeric Reagent | Corresponding Conjugate |
| --- | --- |
| 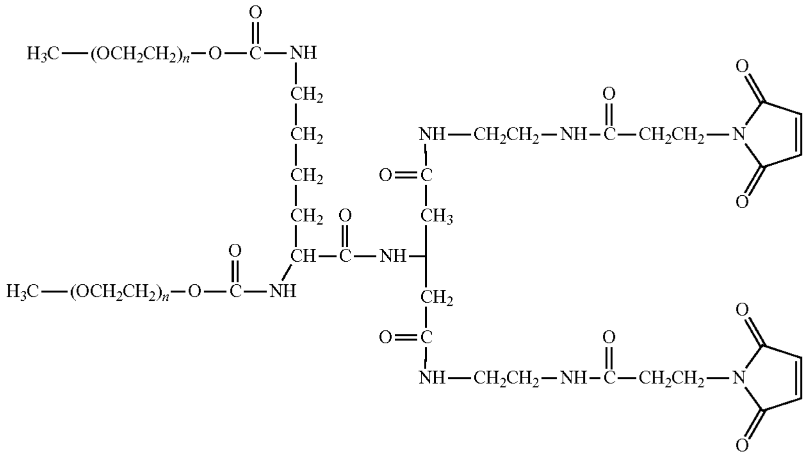<br>Branched mPEG2 Forked Maleimide Derivative | 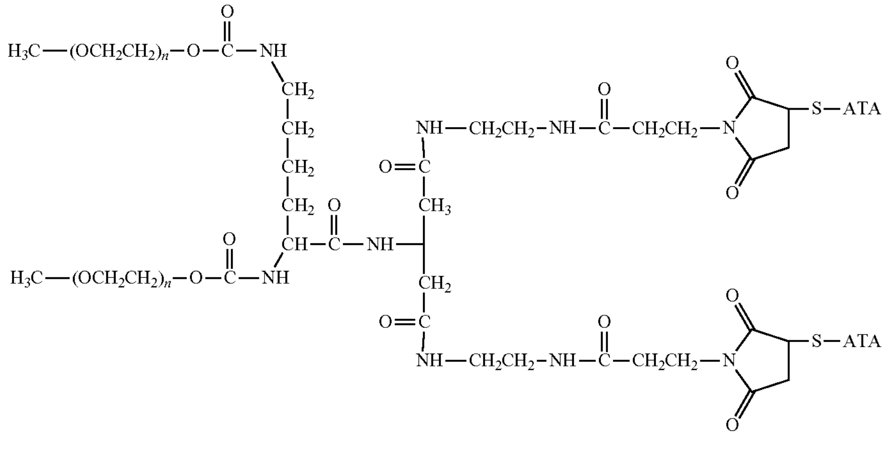<br>Thioether Linkages |
| 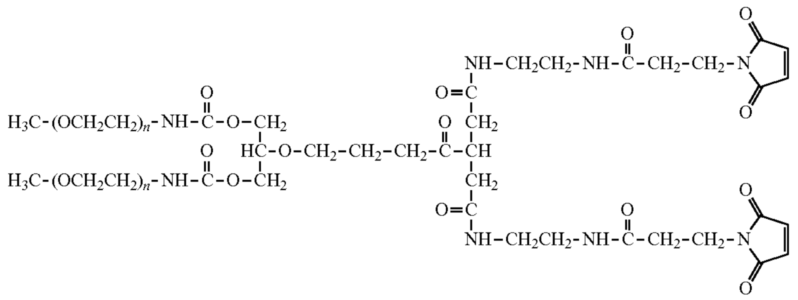<br>Branched mPEG2 Forked Maleimide Derivative | 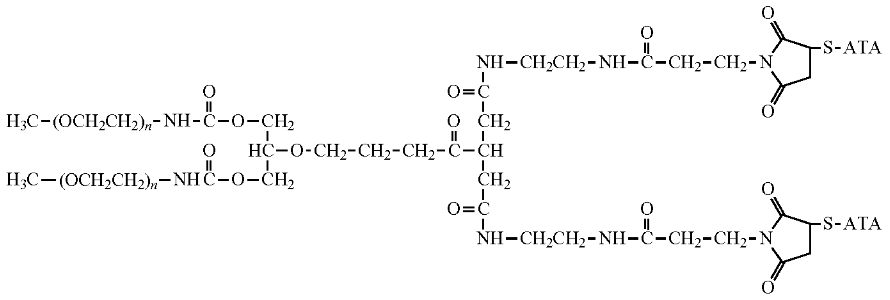<br>Thioether Linkages |
| 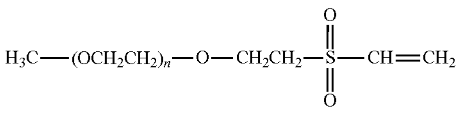<br>mPEG Vinyl Sulfone Derivative | 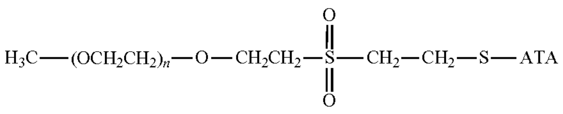<br>Thioether Linkage |

TABLE 3-continued

| Thiol-Specific Polymeric Reagents and the anti-TNFα antibody Conjugate Formed Therefrom | |
|---|---|
| Polymeric Reagent | Corresponding Conjugate |
| 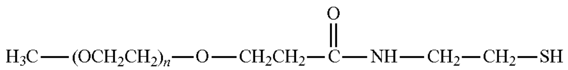 mPEG Thiol Derivative | 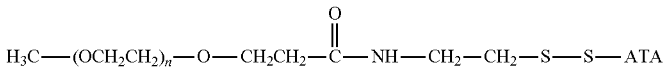 Disulfide Linkage |
| 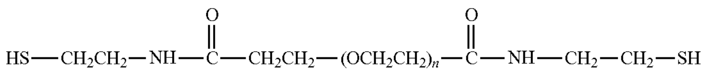 Homobifunctional PEG Thiol Derivative | 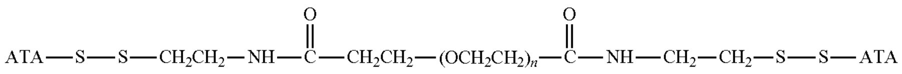 Disulfide Linkages |
| 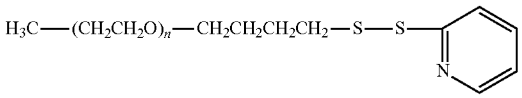 mPEG Disulfide Derivative | $H_3CO—(CH_2CH_2O)_n—CH_2CH_2CH_2CH_2—S—S—ATA$ Disulfide Linkage |
| 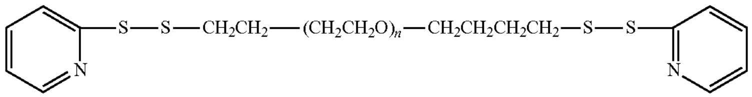 Homobifunctional Disulfide Derivative | $ATA—S—S—CH_2CH_2—(CH_2CH_2O)_n—CH_2CH_2CH_2CH_2—S—S—ATA$ Disulfide Linkages |

With respect to conjugates formed from water-soluble polymers bearing one or more maleimide functional groups (regardless of whether the maleimide reacts with an amine or thiol group on the anti-TNF antibody), the corresponding maleamic acid form(s) of the water-soluble polymer can also react with the anti-TNFα antibody. Under certain conditions (e.g., a pH of about 7-9 and in the presence of water), the maleimide ring will "open" to form the corresponding maleamic acid. The maleamic acid, in turn, can react with an amine or thiol group of an anti-TNFα antibody. Exemplary maleamic acid-based reactions are schematically shown below. POLY represents the water-soluble polymer, and ATA represents the anti-TNFα antibody.

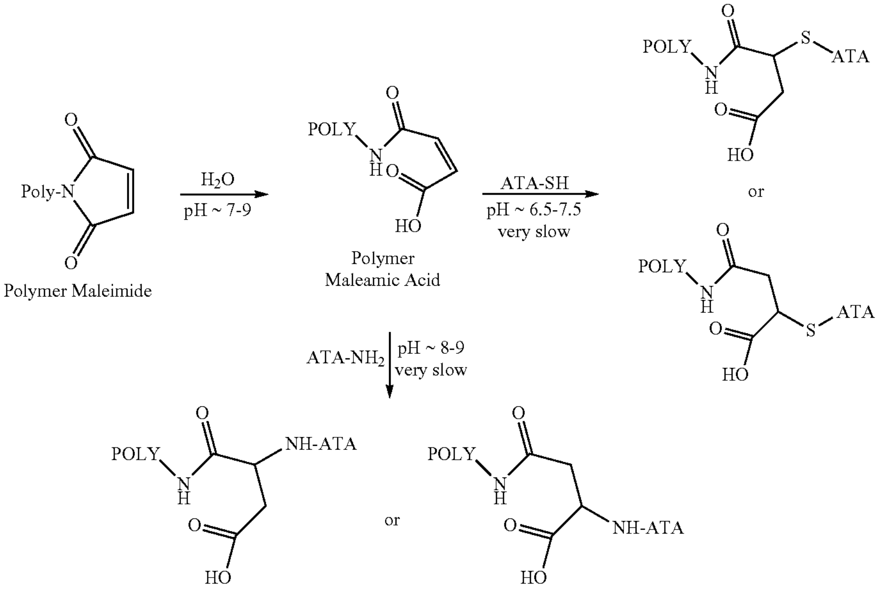

Polymer Maleimide

Polymer Maleamic Acid or or

A representative conjugate in accordance with the invention can have the following structure:

$POLY-L_{0,1}-C(O)Z—Y—S—S-ATA$ wherein POLY is a water-soluble polymer, L is an optional linker, Z is a heteroatom selected from the group consisting of O, NH, and S, and Y is selected from the group consisting of $C_{2-10}$ alkyl, $C_{2-10}$ substituted alkyl, aryl, and substituted aryl, and ATA is an anti-TNFα antibody. Polymeric reagents that can be reacted with an anti-TNFα antibody and result in this type of conjugate are described in U.S. Patent Application Publication No. 2005/0014903.

Conjugates can be formed using thiol-specific polymeric reagents in a number of ways and the invention is not limited in this regard. For example, the anti-TNFα antibody—optionally in a suitable buffer (including amine-containing buffers, if desired)—is placed in an aqueous media at a pH of about 7-8 and the thiol-specific polymeric reagent is added at a molar excess. The reaction is allowed to proceed for about 0.5 to 2 hours, although reaction times of greater than 2 hours (e.g., 5 hours, 10 hours, 12 hours, and 24 hours) can be useful if PEGylation yields are determined to be relatively low. Exemplary polymeric reagents that can be used in this approach are polymeric reagents bearing a reactive group selected from the group consisting of maleimide, sulfone (e.g., vinyl sulfone), and thiol (e.g., functionalized thiols such as an ortho pyridinyl or "OPSS").

With respect to polymeric reagents, those described here and elsewhere can be purchased from commercial sources (e.g., Nektar Therapeutics, Huntsville, Ala.). In addition, methods for preparing the polymeric reagents are described in the literature.

The attachment between the anti-TNFα antibody and the non-peptidic water-soluble polymer can be direct, wherein no intervening atoms are located between the anti-TNF antibody and the polymer, or indirect, wherein one or more atoms are located between the anti-TNF antibody and the polymer. With respect to the indirect attachment, a "spacer moiety" serves as a linker between the residue of anti-TNFα antibody and the water-soluble polymer. The one or more atoms making up the spacer moiety can include one or more of carbon atoms, nitrogen atoms, sulfur atoms, oxygen atoms, and combinations thereof. The spacer moiety can comprise an amide, secondary amine, carbamate, thioether, and/or disulfide group. Nonlimiting examples of specific spacer moieties include those selected from the group consisting of —O—, —S—, —S—S—, —C(O)—, —C(O)—NH—, —NH—C(O)—NH—, —O—C(O)—NH—, —C(S)—, $—CH_2—$, $—CH_2—CH_2—$, $—CH_2—CH_2—CH_2—$, $—CH_2—CH_2—CH_2—CH_2—$, $—O—CH_2—$, $—CH_2—O—$, $—O—CH_2—CH_2—$, $—CH_2—O—CH_2—$, $—CH_2—CH_2—O—$, $—O—CH_2—CH_2—CH_2—$, $—CH_2—O—CH_2—CH_2—$, $—CH_2—CH_2—O—CH_2—$, $—CH_2—CH_2—CH_2—O—$, $—O—CH_2—CH_2—CH_2—CH_2—$, $—CH_2—O—CH_2—CH_2—CH_2—$, $—CH_2—CH_2—O—CH_2—CH_2—$, $—CH_2—CH_2—CH_2—O—CH_2—$, $—CH_2—CH_2—CH_2—CH_2—O—$, $—C(O)—NH—CH_2—$, $—C(O)—NH—CH_2—CH_2—$, $—CH_2—C(O)—NH—CH_2—$, $—CH_2—CH_2—C(O)—NH—$, $—C(O)—NH—CH_2—CH_2—CH_2—$, $—CH_2—C(O)—NH—CH_2—CH_2—$, $—CH_2—CH_2—C(O)—NH—CH_2—$, $—CH_2—CH_2—CH_2—C(O)—NH—$, $—C(O)—NH—CH_2—CH_2—CH_2—CH_2—$, $—CH_2—C(O)—NH—CH_2—CH_2—CH_2—$, $—CH_2—CH_2—C(O)—NH—CH_2—CH_2—$, $—CH_2—CH_2—CH_2—C(O)—NH—CH_2—$, $—CH_2—CH_2—CH_2—C(O)—NH—CH_2—CH_2—$, $—CH_2—CH_2—CH_2—CH_2—C(O)—NH—$, $—C(O)—O—CH_2—$, $—CH_2—C(O)—O—CH_2—$, $—CH_2—CH_2—C(O)—O—$ $CH_2$—, —C(O)—O—$CH_2$—$CH_2$—, —NH—C(O)—$CH_2$—, —$CH_2$—NH—C(O)—$CH_2$—, —$CH_2$—$CH_2$—NH—C(O)—$CH_2$—, —NH—C(O)—$CH_2$—$CH_2$—, —$CH_2$—NH—C(O)—$CH_2$—$CH_2$—, —$CH_2$—$CH_2$—NH—C(O)—$CH_2$—$CH_2$—, —C(O)—NH—$CH_2$—, —C(O)—NH—$CH_2$—$CH_2$—, —O—C(O)—NH—$CH_2$—, —O—C(O)—NH—$CH_2$—$CH_2$—, —NH—$CH_2$—, —NH—$CH_2$—$CH_2$—, —$CH_2$—NH—$CH_2$—, —$CH_2$—$CH_2$—NH—$CH_2$—, —C(O)—$CH_2$—, —C(O)—$CH_2$—$CH_2$—, —$CH_2$—C(O)—$CH_2$—, —$CH_2$—$CH_2$—C(O)—$CH_2$—, —$CH_2$—$CH_2$—C(O)—$CH_2$—$CH_2$—, —$CH_2$—$CH_2$—C(O)—, —$CH_2$—$CH_2$—$CH_2$—C(O)—NH—$CH_2$—$CH_2$—NH—, —$CH_2$—$CH_2$—$CH_2$—C(O)—NH—$CH_2$—$CH_2$—NH—C(O)—, —$CH_2$—$CH_2$—$CH_2$—C(O)—NH—$CH_2$—$CH_2$—NH—C(O)—$CH_2$—, —$CH_2$—$CH_2$—$CH_2$—C(O)—NH—$CH_2$—$CH_2$—NH—C(O)—$CH_2$—$CH_2$—, —O—C(O)—NH—$[CH_2]_h$—$(OCH_2CH_2)_j$—, bivalent cycloalkyl group, —O—, —S—, an amino acid, —$N(R^6)$—, and combinations of two or more of any of the foregoing, wherein $R^6$ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20. Other specific spacer moieties have the following structures: —C(O)—NH—$(CH_2)_{1-6}$—NH—C(O)—, —NH—C(O)—NH—$(CH_2)_{1-6}$—NH—C(O)—, and —O—C(O)—NH—$(CH_2)_{1-6}$—NH—C(O)—, wherein the subscript values following each methylene indicate the number of methylenes contained in the structure, e.g., $(CH_2)_{1-6}$ means that the structure can contain 1, 2, 3, 4, 5 or 6 methylenes. Additionally, any of the above spacer moieties may further include an ethylene oxide oligomer chain comprising 1 to 20 ethylene oxide monomer units [i.e., —$(CH_2CH_2O)_{1-20}$]. That is, the ethylene oxide oligomer chain can occur before or after the spacer moiety, and optionally in between any two atoms of a spacer moiety comprised of two or more atoms. Also, the oligomer chain would not be considered part of the spacer moiety if the oligomer is adjacent to a polymer segment and merely represent an extension of the polymer segment.

Compositions

The conjugates are typically part of a composition. Generally, the composition comprises a plurality of conjugates, preferably although not necessarily, each conjugate is comprised of the same anti-TNFα antibody (i.e., within the entire composition, only one type of anti-TNFα antibody is found). In addition, the composition can comprise a plurality of conjugates wherein any given conjugate is comprised of a moiety selected from the group consisting of two or more different anti-TNFα antibodies (i.e., within the entire composition, two or more different anti-TNFα antibodies are found). Optimally, however, substantially all conjugates in the composition (e.g., 85% or more of the plurality of conjugates in the composition) are each comprised of the same anti-TNFα antibody.

The composition can comprise a single conjugate species (e.g., a monoPEGylated conjugate wherein the single polymer is attached at the same location for substantially all conjugates in the composition) or a mixture of conjugate species (e.g., a mixture of monoPEGylated conjugates where attachment of the polymer occurs at different sites and/or a mixture monPEGylated, diPEGylated and triPEGylated conjugates). The compositions can also comprise other conjugates having four, five, six, seven, eight or more polymers attached to any given moiety having anti-TNFα antibody activity. In addition, the invention includes instances wherein the composition comprises a plurality of conjugates, each conjugate comprising one water-soluble polymer covalently attached to one anti-TNFα antibody, as well as compositions comprising two, three, four, five, six, seven, eight, or more water-soluble polymers covalently attached to one anti-TNFα antibody.

With respect to the conjugates in the composition, the composition will satisfy one or more of the following characteristics: at least about 85% of the conjugates in the composition will have from one to four polymers attached to the anti-TNFα antibody; at least about 85% of the conjugates in the composition will have from one to four polymers attached to the anti-TNFα antibody moiety; at least about 85% of the conjugates in the composition will have from one to three polymers attached to the anti-TNFα antibody moiety; at least about 85% of the conjugates in the composition will have from one to two polymers attached to the anti-TNFα antibody; at least about 85% of the conjugates in the composition will have one polymer attached to the anti-TNFα antibody moiety; at least about 95% of the conjugates in the composition will have from one to five polymers attached to the anti-TNFα antibody moiety; at least about 95% of the conjugates in the composition will have from one to four polymers attached to the anti-TNFα antibody; at least about 95% of the conjugates in the composition will have from one to three polymers attached to the anti-TNFα antibody moiety; at least about 95% of the conjugates in the composition will have from one to two polymers attached to the anti-TNFα antibody; at least about 95% of the conjugates in the composition will have one polymer attached to the anti-TNFα antibody; at least about 99% of the conjugates in the composition will have from one to five polymers attached to the anti-TNFα antibody moiety; at least about 99% of the conjugates in the composition will have from one to four polymers attached to the anti-TNFα antibody; at least about 99% of the conjugates in the composition will have from one to three polymers attached to the anti-TNFα antibody; at least about 99% of the conjugates in the composition will have from one to two polymers attached to the anti-TNFα antibody; and at least about 99% of the conjugates in the composition will have one polymer attached to the anti-TNFα antibody.

In one or more embodiments, it is preferred that the conjugate-containing composition is free or substantially free of albumin. It is also preferred that the composition is free or substantially free of proteins that do not have anti-TNFα antibody. Thus, it is preferred that the composition is 85%, more preferably 95%, and most preferably 99% free of albumin. Additionally, it is preferred that the composition is 85%, more preferably 95%, and most preferably 99% free of any protein that does not have anti-TNF antibody activity. To the extent that albumin is present in the composition, exemplary compositions of the invention are substantially free of conjugates comprising a poly(ethylene glycol) polymer linking a residue of an anti-TNFα antibody to albumin.

Control of the desired number of polymers for any given moiety can be achieved by selecting the proper polymeric reagent, the ratio of polymeric reagent to the anti-TNFα antibody moiety, temperature, pH conditions, and other aspects of the conjugation reaction. In addition, reduction or elimination of the undesired conjugates (e.g., those conjugates having four or more attached polymers) can be achieved through purification means.

For example, the polymer-anti-TNFα antibody conjugates can be purified to obtain/isolate different conjugated species. Specifically, the product mixture can be purified to obtain an average of anywhere from one, two, three, four, five or more PEGs per anti-TNF antibody, typically one, two or three PEGs per anti-TNFα antibody. The strategy for purification of the final conjugate reaction mixture will depend upon a number of factors, including, for example, the molecular weight of the polymeric reagent employed, the particular anti-TNFα antibody, the desired dosing regimen, and the residual activity and in vivo properties of the individual conjugate(s).

If desired, conjugates having different molecular weights can be isolated using gel filtration chromatography and/or ion exchange chromatography. That is to say, gel filtration chromatography is used to fractionate differently numbered polymer-to-anti-TNFα antibody ratios (e.g., 1-mer, 2-mer, 3-mer, and so forth, wherein "1-mer" indicates 1 polymer to anti-TNFα antibody, "2-mer" indicates two polymers to anti-TNFα antibody moiety, and so on) on the basis of their differing molecular weights (where the difference corresponds essentially to the average molecular weight of the water-soluble polymer portion). For example, in an exemplary reaction where a 35,000 Dalton protein is randomly conjugated to a polymeric reagent having a molecular weight of about 20,000 Daltons, the resulting reaction mixture may contain unmodified protein (having a molecular weight of about 35,000 Daltons), monoPEGylated protein (having a molecular weight of about 55,000 Daltons), diPEGylated protein (having a molecular weight of about 75,000 Daltons), and so forth.

While this approach can be used to separate PEG and other polymer-anti-TNFα antibody moiety conjugates having different molecular weights, this approach is generally ineffective for separating positional isoforms having different polymer attachment sites within the anti-TNFα antibody moiety. For example, gel filtration chromatography can be used to separate from each other mixtures of PEG 1-mers, 2-mers, 3-mers, and so forth, although each of the recovered conjugate compositions may contain PEG(s) attached to different reactive groups (e.g., lysine residues) within the anti-TNFα antibody.

Gel filtration columns suitable for carrying out this type of separation include Superdex™ and Sephadex™ columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) absorbance at 280 nm for protein content, (ii) dye-based protein analysis using bovine serum albumin (BSA) as a standard, (iii) iodine testing for PEG content (Sims et al. (1980) *Anal. Biochem,* 107:60-63), (iv) sodium dodecyl sulfate polyacrylamide gel electrophoresis (SDS AGE), followed by staining with barium iodide, and (v) high performance liquid chromatography (HPLC).

Separation of positional isoforms is carried out by reverse phase chromatography using a reverse phase-high performance liquid chromatography (RP-HPLC) using a suitable column (e.g., a C18 column or C3 column, available commercially from companies such as Amersham Biosciences or Vydac) or by ion exchange chromatography using an ion exchange column, e.g., a Sepharose™ ion exchange column available from Amersham Biosciences. Either approach can be used to separate polymer-active agent isomers having the same molecular weight (i.e., positional isoforms).

The compositions are preferably substantially free of proteins that do not have anti-TNFα antibody activity. In addition, the compositions preferably are substantially free of all other noncovalently attached water-soluble polymers. In some circumstances, however, the composition can contain a mixture of polymer-anti-TNFα antibody conjugates and unconjugated anti-TNFα antibody.

Optionally, the composition of the invention further comprises a pharmaceutically acceptable excipient. If desired, the pharmaceutically acceptable excipient can be added to a conjugate to form a composition.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The composition can also include an antimicrobial agent for preventing or deterring microbial growth. Nonlimiting examples of antimicrobial agents suitable for one or more embodiments of the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the conjugate or other components of the preparation. Suitable antioxidants for use in one or more embodiments of the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate (i.e., the conjugate formed between the active agent and the polymeric reagent) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The compositions encompass all types of formulations and in particular those that are suited for injection, e.g., powders or lyophilates that can be reconstituted as well as liquids. Examples of suitable diluents for reconstituting solid compositions prior to injection include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned.

The compositions of one or more embodiments of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

The invention also provides a method for administering a conjugate as provided herein to a patient suffering from a condition that is responsive to treatment with conjugate. The method comprises administering to a patient, generally via injection, a therapeutically effective amount of the conjugate (preferably provided as part of a pharmaceutical composition). As previously described, the conjugates can be administered parenterally by intravenous injection. Advantageously, the conjugate can also be administered by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The method of administering may be used to treat any condition that can be remedied or prevented by administration of the conjugate. Those of ordinary skill in the art appreciate which conditions a specific conjugate can effectively treat. For example, the conjugates can be used either alone or in combination with other pharmacotherapy to treat patients suffering arthritis, Crohn's disease, psoriatic arthritis, ulcerative colitis, plaque psoriasis, sarcoidosis, ankylosing spondylitis, and cytokine-induced islet destruction in autoimmune diabetes. Advantageously, the conjugate can be administered to the patient prior to, simultaneously with, or after administration of another active agent.

The actual dose to be administered will vary depending upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day. A given dose can be periodically administered up until, for example, symptoms of arthritis lessen and/or are eliminated entirely.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration once daily, three times weekly, twice weekly, once weekly, twice monthly, once monthly, and any combination thereof. Once the clinical endpoint has been achieved, dosing of the composition is halted.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All articles, books, patents and other publications referenced herein are hereby incorporated by reference in their entireties.

EXAMPLES

The practice of the invention will employ, unless otherwise indicated, conventional techniques of organic synthesis, biochemistry, protein purification and the like, which are within the skill of the art. Such techniques are fully explained in the literature. See, for example, J. March, Advanced Organic Chemistry: Reactions Mechanisms and Structure, 4th Ed. (New York: Wiley-Interscience, 1992), supra.

In the following examples, efforts have been made to ensure accuracy with respect to numbers used (e.g., amounts, temperatures, etc.) but some experimental error and deviation should be taken into account. Unless indicated otherwise, temperature is in degrees C. and pressure is at or near atmospheric pressure at sea level. Each of the following examples is considered to be instructive to one of ordinary skill in the art for carrying out one or more of the embodiments described herein.

Infliximab was purchased commercially from a pharmaceutical distributor as a lyophilized powder and was reconstituted immediately prior to use with sterile water to yield a reconstituted stock infliximab liquid at a concentration of 10 mg/mL and thereafter stored at 4° C.

SDS-PAGE Analysis

In some instances, samples were analyzed by sodium dodecyl sulfate-polyacrylamide gel electrophoresis (SDS-PAGE) using an Invitrogen system (SureLock II Precast Gel Electrophoresis System). Samples were mixed with sample buffer. Then, the prepared samples were loaded onto a gel and run for approximately thirty minutes.

Anion Exchange Chromatography

In some instances, a Hitrap Q Sepharose HP anion exchange column (5 ml, Amersham Biosciences) was used with the AKTAprime system (Amersham Biosciences) to purify the prepared conjugates. For each conjugate solution prepared, the conjugate was loaded on a column that is pre-equilibrated in 50 mM MES buffer, pH 5.4 (buffer A) and is then washed with nine column volumes of buffer A to remove any unreacted PEG reagent. Subsequently, a gradient of buffer A with 0-100% buffer B (50 mM IVIES with 0.5 M NaCl buffer, pH 5.4) was raised. The eluent was monitored by UV detector at 280 nm. Any higher-mers (e.g., 11-mers, 10-mers, and so forth) will elute first, followed by increasingly smaller and smaller conjugates (e.g., 5-mers and 4-mers, and so forth), until 1-mers, and finally, unconjugated infliximab species elute. The fractions can be pooled and the purity of the individual conjugate was determined by SEC-HPLC mostly by SDS-PAGE.

SEC-HPLC Analysis

In some instances, size exclusion chromatography (SEC-HPLC) analysis was performed on an Agilent 1100 HPLC system (Agilent). Samples are analyzed using a GF-450 Zorbax (Agilent), and a mobile phase consisting of 90% phosphate buffered saline and 10% ethanol, pH 7.2. The flow rate for the column can be 0.5 ml/min. Eluted protein and PEG-protein conjugates can be detected using UV at 280 nm.

Example 1

PEGylation of Infliximab with mPEG-SPA, 30 kDa

10:1 Polymer to Infliximab Ratio

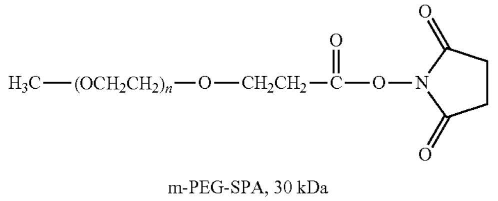

m-PEG-SPA, 30 kDa mPEG-SPA, 30 kDa, stored at −20° C. under argon, was warmed to ambient temperature. A ten-fold excess (relative to the amount of infliximab in a measured aliquot of the stock infliximab liquid) of the warmed mPEG-SPA was dissolved in buffer 2 mM HCL (<10% the reaction volume) and is added to an aliquot of the stock infliximab liquid and mixed well. After the addition of the mPEG-SPA, the pH of the reaction mixture is determined and adjusted to pH 7.2-7.5 using conventional techniques. To allow for coupling of the mPEG-SPA to infliximab via an amide linkage, the reaction solution is stirred for five hours at room temperature and thereafter is stirred overnight at 3-8° C. in a cold room in the dark, thereby resulting in a conjugate solution. The reaction was quenched with glycine.

According to SDS-PAGE analysis, approximately 45% PEGylation occurred, which consisted mostly of 1-mers, 2-mers, 3-mers and some 4-mers.

Using this same approach, other conjugates can be prepared using mPEG-SPA having other weight average molecular weights.

Example 2

Example 1 was repeated and served as a control for Example 2b

Example 2b

PEGylation of Infliximab with mPEG-SPA, 30 kDa

10:1 Polymer to Infliximab Ratio, with Blocking Agent

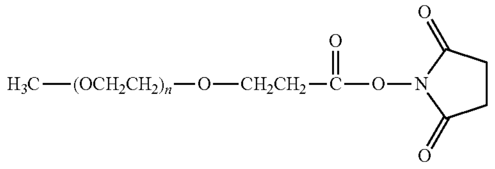

mPEG-SPA, 30 kDa

Prior to the conjugation reaction, 0.164 mg of infliximab in sterile water was obtained and pH tested and adjusted to 8.0. To reversibly protect the most reactive amino groups in infliximab, this liquid was combined with a 10-fold molar excess of dimethylmaleic anhydride, "DMMAn", (Tsunoda, S., et al., *J. Pharmacol. Exp. Ther.* 1999, 290, 368-72) relative to moles of infliximab, to thereby form a DMMAn-treated infliximab liquid. The protection reactions were allowed to proceed for 30 minutes at 37° C. The pH was tested and adjusted as necessary to ensure a pH of 8.0.

mPEG-SPA, 30 kDa, stored at −20° C. under argon, was warmed to ambient temperature. The mPEG-SPA, 30 kDa, (1.4 mg) was dissolved in 11.6 μL of 2 mM HCl to form an mPEG-SPA solution. The mPEG-SPA solution was added to the DMMAn-treated infliximab liquid (pH 8.0, room temperature), until a ten-fold molar excess of mPEG-SPA relative to infliximab was reached. To allow for coupling of the mPEG-SPA to infliximab via an amide linkage, the reaction solution was stirred for two hours at room temperature and then overnight (16 hours) at 6° C., thereby resulting in a conjugate solution. The reaction was quenched by addition of glycine. Thereafter, to deprotect the protected lysine amino groups, the reaction mixture was adjusted to pH 6.0 with 0.1 N HCl and incubated at 37° C. for 30 minutes.

According to SDS-PAGE analysis, approximate 20% monoPEGylation occurred.

Using this same approach, other conjugates can be prepared using mPEG-SPA having other weight average molecular weights.

Example 3a

PEGylation of Infliximab with Branched mPEG2-N-Hydroxysuccinimide, 60 kDa

10:1 Polymer to Infliximab Ratio

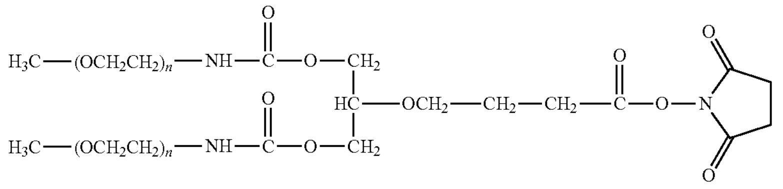

Branched mPEG2-N-Hydroxysuccinimide, 60 kDa

Branched mPEG2-N-hydroxysuccinimide, 60 kDa, stored at −20° C. under argon, was warmed to ambient temperature. The branched mPEG2-N-hydroxysuccinimide (0.326 mg) was dissolved in 32.6 μL of 2 mM HCl to form a branched mPEG2-N-hydroxysuccinimide solution. The branched mPEG2-N-hydroxysuccinimide solution was added to a previously prepared infliximab reaction mixture of 164 μg until a ten-fold molar excess of the branched mPEG2-N-hydroxysuccinimide to infliximab was reached. The pH was tested and adjusted as necessary to ensure a pH of 8.0. To allow for coupling of the branched mPEG2-N-hydroxysuccinimide to infliximab via an amide linkage, the reaction solution was stirred for two hours at room temperature and then overnight (sixteen hours) at 6° C., thereby resulting in a conjugate solution. The reaction was quenched by addition of glycine and the pH was reduced to a pH of 6.0.

According to SDS-PAGE analysis, approximately 40% of the native was conjugated to PEG. The reaction yielded mostly 1-mers and some 2-mers and 3-mers.

Using this same approach, other conjugates can be prepared using branched mPEG2-N-hydroxysuccinimide having other weight average molecular weights.

Example 3b

PEGylation of Infliximab with Branched mPEG2-N-Hydroxysuccinimide, 60 kDa

10:1 Polymer to Infliximab Ratio, with Blocking Agent

Prior to the conjugation reaction, 0.164 mg of infliximab in sterile water was obtained and pH tested and adjusted to 8.0. To reversibly protect the most reactive amino groups in infliximab, this liquid was combined with a ten-fold molar excess of dimethylmaleic anhydride, "DMMAn", (Tsunoda, S., et al., *J. Pharmacol. Exp. Ther.* 1999, 290, 368-72) relative to moles of infliximab, to thereby form a DMMAn-treated infliximab liquid. The protection reactions were allowed to proceed for 30 minutes at 37° C. The pH was tested and adjusted as necessary to ensure a pH of 8.0.

Branched mPEG2-N-hydroxysuccinimide, 60 kDa, stored at −20° C. under argon, was warmed to ambient temperature. The branched mPEG2-N-hydroxysuccinimide, 60 kDa, (0.326 mg) was dissolved in 32.6 μL of 2 mM HCl to form a branched mPEG2-N-hydroxysuccinimide solution. The branched mPEG2-N-hydroxysuccinimide solution was added to the DMMAn-treated infliximab liquid (pH 8.0, room temperature), until a ten-fold molar excess of branched mPEG2-N-hydroxysuccinimide relative to infliximab was reached. To allow for coupling of the branched mPEG2-N-hydroxysuccinimide to infliximab via an amide linkage, the reaction solution was stirred for two hours at room temperature and thereafter stirred overnight (sixteen hours) at 6° C., thereby resulting in a conjugate solution. The reaction was quenched by addition of glycine. Thereafter, to deprotect the protected lysine amino groups, the reaction mixture was adjusted to pH 6.0 with 0.1 N HCl and incubated at 37° C. for 30 minutes.

According to SDS-PAGE analysis, approximately 20% of the native infliximab was conjugate to PEG. The reaction yield mostly 1-mers and some 2-mers.

Using this same approach, other conjugates can be prepared using branched mPEG2-N-hydroxysuccinimide having other weight average molecular weights.

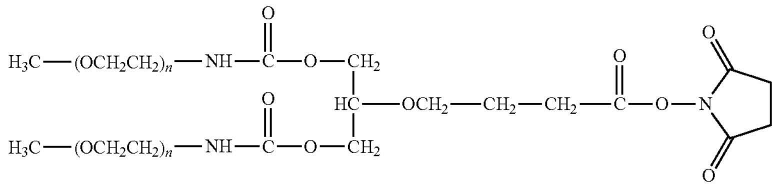

Branched mPEG2-N-Hydroxysuccinimide, 60 kDa

Example 4a (Unreduced)

PEGylation of Infliximab with mPEG-MAL, 30 kDa

10:1 Polymer to Infliximab Ratio

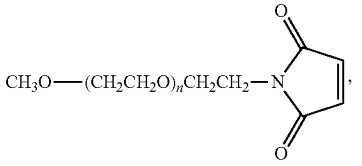

mPEG-MAL, 30 kDa

This reaction was to use as a control for Example 4b. By not reducing the infliximab, it was possible to identify whether there were any free thiol groups associated with the side chains of cysteine residues.

Prior to the conjugation reaction, 0.164 mg of infliximab in sterile water was obtained. To this was added mPEG-MAL, 30 kDa, (previously stored at −20° C. under argon, warmed to ambient temperature, 0.328 mg of which was dissolved in 0.1 mL of 2 mM HCl) until a ten-fold molar excess of mPEG-MAL to infliximab was reached. To allow for conjugation, the mixture was stirred at room temperature for three hours.

According to SDS-PAGE analysis, less than 10% of 1-mer conjugates were detected.

Using this same approach, other conjugates can be prepared using mPEG-MAL having other weight average molecular weights.

Example 4b

PEGylation of Infliximab with mPEG-MAL, 30 kDa

10:1 Polymer to Infliximab Ratio, DTT (Reducing Agent)

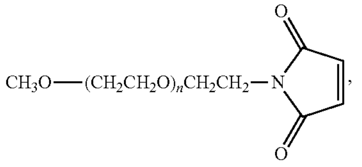

mPEG-MAL, 30 kDa

In most cases, reducing an antibody will create a fragment that cannot be returned to a similar conformation after PEGylation. In any event, this reaction was performed to compare the number of free cysteine residues prior to reduction to the number of free cysteine residues following reduction.

Prior to the conjugation reaction, 0.164 mg of infliximab in sterile water was obtained. To this was added 1.68 mg of DTT (in a ten-fold excess relative to moles of infliximab) to allow for reduction at room temperature for one hour. The DTT was then removed via DeSalt media and concentrated back down to ~1 mL of stock solution with a 30K Mw cutoff membrane to form a reduced stock infliximab liquid.

mPEG-MAL, 30 kDa, stored at −20° C. under argon was warmed to ambient temperature. The warmed mPEG-MAL (0.328 mg) was dissolved in 0.1 mL of 2 mM HCl to form an mPEG-MAL solution. To the reduced stock infliximab liquid was added the mPEG-MAL solution to result in a ten-fold molar excess of mPEG-MAL. The mixture was stirred at room temperature for three hours.

According to SDS-PAGE analysis, 1-mers (about 20%) and 2-mers (about 5%) were detected.

Using this same approach, other conjugates can be prepared using mPEG-MAL having other weight average molecular weights.

Example 5

PEGylation of Infliximab with mPEG-SMB, 30 kDa

200:1 Polymer to Infliximab Ratio

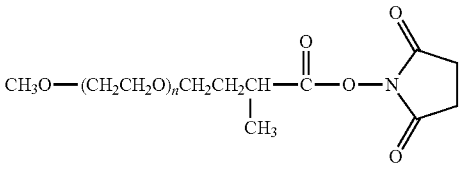

mPEG-SMB, 30 kDa mPEG-SMB, 30 kDa, stored at −20° C. under argon, was warmed to ambient temperature. The warmed mPEG-SMB (6.56 mg) was dissolved in 0.2 mL of 2 mM HCl to form an mPEG-SMB solution. The mPEG-SMB solution was added to an aliquot of the stock infliximab liquid containing 0.164 mg of infliximab until a 200 molar excess of mPEG-SMB relative to infliximab was reached. After the addition of the mPEG-SMB, the pH of the reaction mixture was tested to ensure a pH of 7.2 to 7.5. To allow for coupling of the mPEG-SMB to infliximab via an amide linkage, the reaction solution was stirred for three hours at room temperature. Coupling was allowed to continue by stirring the reaction solution overnight (sixteen hours) at 6° C., thereby resulting in a conjugate solution. The reaction was quenched with glycine.

According to SDS-PAGE analysis, 1-mers (about 40%) and 2-mers, 3-mers and 4-mers (totaling about 20%) were detected.

Using this same approach, other conjugates can be prepared using mPEG-SMB having other weight-average molecular weights.

Example 6

Selective N-Terminal PEGylation of Infliximab with Linear mPEG-Butyraldehyde, 30 kDa 200:1 Polymer to Infliximab Ratio

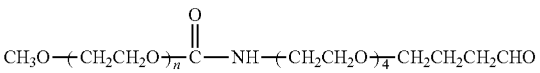

Linear mPEG-Butyraldehyde Derivative, 30 kDa (“mPEG-ButyrALD”)

mPEG-Butyraldehyde, 30 kDa, stored at −20° C. under argon, was warmed to ambient temperature. The mPEG-butyraldehyde (6.56 mg) was dissolved in 0.2 mL of 2 mM HCl to form an mPEG-butyraldehyde solution. The mPEG-butryaldehyde solution was added to a previously prepared infliximab reaction mixture (0.164 mg stock infliximab liquid, pH adjusted to 6.0 via conventional methods) until a 200 molar excess of mPEG-butryaldehyde to infliximab was reached. After addition of the mPEG-butyraldehyde, the pH was tested and adjusted as necessary to ensure a pH of about 6.0. A reducing agent, $NaCNBH_3$, was added at a five-fold molar excess relative to the branched mPEG-butyraldehyde (with the pH tested and adjusted as necessary to ensure a pH of about 6.0). The solution was then stirred for two hours at room temperature and then overnight at 4° C. to ensure coupling via an amine linkage.

According to SDS-PAGE analysis, 1-mers (about 40%) and 2-mers and 3-mers (totaling about 10%) were detected.

According to SDS-PAGE analysis, 1-mers (about 40%) and 2-mers and 3-mers (totaling about 10%) were detected. It is noted that N-terminal PEGylation could decrease the conjugate's ability to find to TNFα; binding activity assays for the resulting conjugate are particularly warranted.

Using this same approach, other conjugates can be prepared using mPEG-butyraldehyde having other weight average molecular weights.

Example 7

PEGylation of Infliximab with mPEG-PIP, 20 kDa

200:1 Polymer to Infliximab Ratio

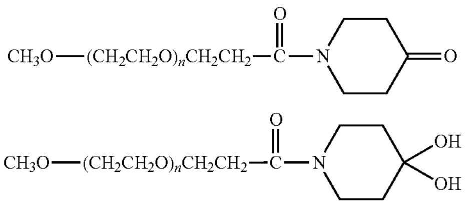

mPEG-PIP, 20 kDa (ketone and acetal forms)

mPEG-PIP, 20 kDa, stored at −20° C. under argon, was warmed to ambient temperature. The mPEG-PIP (4.4 mg) was dissolved in 0.2 mL of 2 mM HCl to form an mPEG-PIP solution. The mPEG-PIP solution was added to a previously prepared infliximab reaction mixture (0.164 mg stock infliximab liquid, pH adjusted to 6.0 via conventional methods) until a 200 molar excess of mPEG-PIP to infliximab was reached. After addition of the mPEG-PIP, the pH was tested and adjusted as necessary to ensure a pH of about 6.0. A reducing agent, $NaCNBH_3$, was added at a five-fold molar excess relative to the mPEG-PIP (with the pH tested and adjusted as necessary to ensure a pH of about 6.0). The solution was then stirred for two hours at room temperature and then overnight at 4° C. to ensure coupling via an amine linkage.

According to SDS-PAGE analysis, about 10% of 1-mer conjugates were detected.

Example 8a

PEGylation of Infliximab with Branched mPEG2-N-Hydroxysuccinimide, 40 kDa

200:1 Polymer to Infliximab Ratio

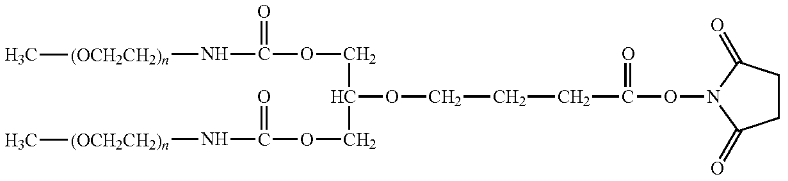

Branched mPEG2-N-Hydroxysuccinimide, 40 kDa

Branched mPEG2-N-hydroxysuccinimide, 40 kDa, stored at −20° C. under argon, was warmed to ambient temperature. The branched mPEG2-N-hydroxysuccinimide (8.7 mg) was dissolved in 200 μL of 2 mM HCl to form a branched mPEG2-N-hydroxysuccinimide solution. The branched mPEG2-N-hydroxysuccinimide solution was added to a previously prepared infliximab reaction mixture (0.164 mg stock infliximab liquid, pH 8.0) until a 200-fold molar excess of the branched mPEG2-N-hydroxysuccinimide to infliximab was reached. The pH was tested and adjusted as necessary to ensure a pH of 8.0. To allow for coupling of the branched mPEG2-N-hydroxysuccinimide to infliximab via an amide linkage, the reaction solution was stirred for two hours at room temperature and then overnight (sixteen hours) at 6° C., thereby resulting in a conjugate solution. The pH was reduced to 6.0 with 0.1 M HCl to release the anhydride. The reaction was quenched by addition of glycine. According to SDS-PAGE analysis, about 10% of 1-mer conjugates were detected.

According to SDS-PAGE analysis, about ~30% of 1-mer conjugates were detected.

Using this same approach, other conjugates can be prepared using branched mPEG2-N-hydroxysuccinimide having other weight average molecular weights.

Example 8b

PEGylation of Infliximab with Branched mPEG2-N-Hydroxysuccinimide, 40 kDa

200:1 Polymer to Infliximab Ratio, with Blocking Agent

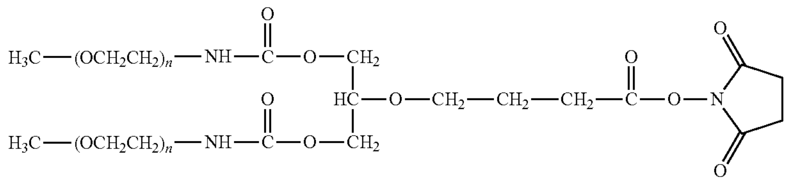

Branched mPEG2-N-Hydroxysuccinimide, 40 kDa

Prior to the conjugation reaction, 0.164 mg of infliximab in sterile water was obtained and pH tested and adjusted to 8.0. To reversibly protect the most reactive amino groups in infliximab, this liquid was combined with a ten-fold molar excess of dimethylmaleic anhydride, "DMMAn", (13.8 mg) (Tsunoda, S., et al., *J. Pharmacol. Exp. Ther.* 1999, 290, 368-72) relative to moles of infliximab, to thereby form a DMMAn-treated infliximab liquid. The protection reactions were allowed to proceed for 30 minutes at 37° C. The pH was tested and adjusted as necessary to ensure a pH of 8.0.

Branched mPEG2-N-hydroxysuccinimide, 40 kDa, stored at −20° C. under argon, was warmed to ambient temperature. The branched mPEG2-N-hydroxysuccinimide, 40 kDa, (8.7 mg) was dissolved in 32.6 μL of 2 mM HCl to form a branched mPEG2-N-hydroxysuccinimide solution. The branched mPEG2-N-hydroxysuccinimide solution was added to the DMMAn-treated infliximab liquid (pH 8.0, room temperature), until a 200-fold molar excess of branched mPEG2-N-hydroxysuccinimide relative to infliximab was reached. To allow for coupling of the branched mPEG2-N-hydroxysuccinimide to infliximab via an amide linkage, the reaction solution was stirred for two hours at room temperature and thereafter stirred overnight (sixteen hours) at 6° C., thereby resulting in a conjugate solution. The reaction was quenched by addition of glycine. Thereafter, to deprotect the protected lysine amino groups, the reaction mixture was adjusted to pH 6.0 with 0.1 N HCl and incubated at 37° C. for 30 minutes.

According to SDS-PAGE analysis, approximately 10% of 1-mers were detected.

Using this same approach, other conjugates can be prepared using branched mPEG2-N-hydroxysuccinimide having other weight average molecular weights.

Using this same approach, other conjugates can be prepared using branched mPEG2-N-hydroxysuccinimide having other weight average molecular weights.

Example 9

Scale Up of Example 5 mPEG-SMB, 30 kDa, stored at −20° C. under argon, was warmed to ambient temperature. The warmed mPEG-SMB (65.6 mg) was dissolved in 2.0 mL of 2 mM HCl to form an mPEG-SMB solution. The mPEG-SMB solution was added to an aliquot of the stock infliximab suspension containing 1.64 mg of infliximab until a 200 molar excess of mPEG-SMB relative to infliximab was reached. After the addition of the mPEG-SMB, the pH of the reaction mixture was tested to ensure a pH of 7.2 to 7.5. To allow for coupling of the mPEG-SMB to infliximab via an amide linkage, the reaction solution was stirred for three hours at room temperature. Coupling was allowed to continue by stirring the reaction solution overnight (sixteen hours) at 6° C., thereby resulting in a conjugate solution. The reaction was quenched with glycine.

According to SDS-PAGE analysis, 1-mers (about 40%) and 2-mers and 3-mers (totaling about 20%) were detected.

Example 10

Scale Up of Example 8A

Example 8A was carried out again, but on larger scale. The results and yield were similar.

Example 11

PEGylation of Infliximab with mPEG-SPA, 5 kDa

20:1 Polymer to Infliximab Ratio

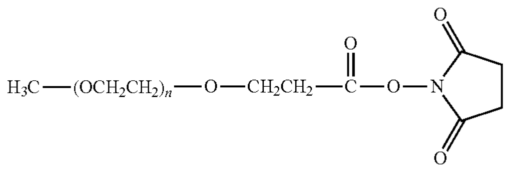

mPEG-SPA, 5 kDa mPEG-SPA, 5 kDa, stored at −20° C. under argon, was warmed to ambient temperature. A twenty-fold excess (relative to the amount of infliximab in a measured aliquot of the stock infliximab suspension) of the warmed mPEG-SPA was dissolved in buffer (164 μl of 1 mg/mL PEG solution in 2 mM HCl) and is added to an aliquot of the stock infliximab liquid (0.246 mg infliximab) and mixed well. After the addition of the mPEG-SPA, the pH of the reaction mixture is determined and adjusted to 7.2-7.5 using conventional techniques. To allow for coupling of the mPEG-SPA to infliximab via an amide linkage, the reaction solution is stirred for five hours at room temperature in the dark and thereafter is stirred overnight at 3-8° C. in a cold room in the dark, thereby resulting in a conjugate solution. The reaction was quenched with glycine.

PEGylation yields were not determined given the relatively small difference in change of molecular weights between the unconjugated and conjugated forms.

Using this same approach, other conjugates are prepared using mPEG-SPA having other weight average molecular weights.

Example 12

PEGylation of Infliximab with Branched mPEG2-N-Hydroxysuccinimide, 60 kDa

20:1 Polymer to Infliximab Ratio

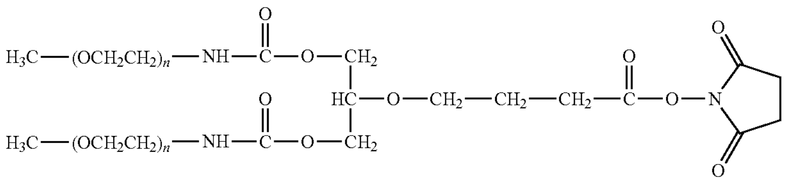

Branched mPEG2-N-Hydroxysuccinimide, 60 kDa

Branched mPEG2-N-hydroxysuccinimide, 60 kDa, stored at −20° C. under argon, was warmed to ambient temperature. The branched mPEG2-N-hydroxysuccinimide (0.650 mg) was dissolved in 32.6 μL of 2 mM HCl to form a branched mPEG2-N-hydroxysuccinimide solution. The branched mPEG2-N-hydroxysuccinimide solution was added to a previously prepared infliximab reaction mixture of 164 μg (raising the pH to 7.0 by conventional methods) until a ten-fold molar excess of the branched mPEG2-N-hydroxysuccinimide to infliximab was reached. The pH was tested and adjusted as necessary to ensure a pH of 7.0. To allow for coupling of the branched mPEG2-N-hydroxysuccinimide to infliximab via an amide linkage, the reaction solution was stirred for two hours at room temperature and then overnight (sixteen hours) at 6° C., thereby resulting in a conjugate solution. The reaction was quenched by addition of glycine.

According to SDS-PAGE analysis, approximately 20% of the native was conjugated to PEG. The reaction yielded mostly 1-mers and some 2-mers.

Using this same approach, other conjugates can be prepared using branched mPEG2-N-hydroxysuccinimide having other weight average molecular weights.

Example 13

PEGylation of Infliximab with a Branched mPEG-MAL, 60 kDa ("mPEG2-MAL")

20:1 Polymer to Infliximab Ratio

In most cases, reducing an antibody will create a fragment that cannot be returned to a similar conformation after PEGylation. In any event this reaction was performed to compare the number of free cysteine residues prior to reduction to the number of free cysteine residues following reduction.

Prior to the conjugation reaction, 01.64 mg of infliximab in sterile water was obtained. To this was added 1.68 mg of DTT (in a ten fold excess relative to moles of infliximab) to allow for reduction at room temperature for one hour. The DTT was then removed via DeSalt media and concentrated back down to −1 mL of stock solution with a 30K Mw cutoff membrane to form a reduced stock infliximab liquid.

Branched mPEG-MAL, 60 kDa, stored at −20° C. argon was warmed to ambient temperature. The warmed branched mPEG-MAL (0.652 μg) was dissolved in 0.1 mL of 2 mM HCl to form a branched mPEG-MAL solution. To a reduced stock infliximab liquid was added the branched mPEG-MAL solution to result in a twenty-fold molar excess of mPEG-MAL. The mixture was stirred at room temperature for three hours.

According to SDS-PAGE analysis, 1-mers (about 20%) were formed.

Using this same approach, other conjugates can be prepared using mPEG-MAL having other weight average molecular weights.

Example 14

PEGylation of Infliximab with Branched mPEG2-N-Hydroxysuccinimide, 60 kDa

Two×20:1 Polymer to Infliximab Ratio

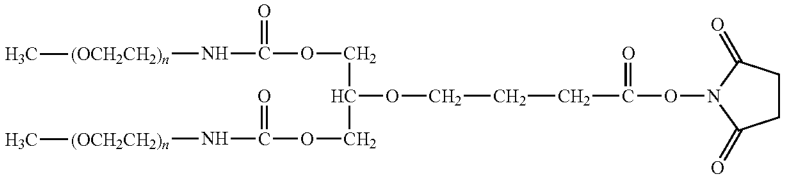

Branched mPEG2-N-Hydroxysuccinimide, 60 kDa

Branched mPEG2-N-hydroxysuccinimide, 60 kDa, stored at −20° C. under argon, was warmed to ambient temperature. The branched mPEG2-N-hydroxysuccinimide (0.650 mg) was dissolved in 32.6 μL of 2 mM HCl to form a branched mPEG2-N-hydroxysuccinimide solution. The branched mPEG2-N-hydroxysuccinimide solution was added to an aliquot of the stock infliximab liquid (164 μg of infliximab) (stock infliximab liquid pH adjusted to 7.0 using conventional methods) until a twenty-fold molar excess of the branched mPEG2-N-hydroxysuccinimide to infliximab was reached. The pH was tested and adjusted as necessary to ensure a pH of 7.0. The solution reacted for 30 minutes and then a second addition of mPEG2-N-hydroxysuccinimide solution was prepared and added in the same manner as before. To allow for coupling of the branched mPEG2-N-hydroxysuccinimide to infliximab via an amide linkage, the reaction solution was stirred for two hours at room temperature and then overnight (sixteen hours) at 6° C., thereby resulting in a conjugate solution. The reaction was quenched by addition of glycine.

According to SDS-PAGE analysis, approximately 30% of the native was conjugated to PEG. The reaction yielded mostly 1-mers and some 2-mers.

Using this same approach, other conjugates can be prepared using branched mPEG2-N-hydroxysuccinimide having other weight average molecular weights.

Example 15

PEGylation of Infliximab with Branched mPEG2-N-Hydroxysuccinimide, 60 kDa

(Two×10):1 Polymer to Infliximab Ratio

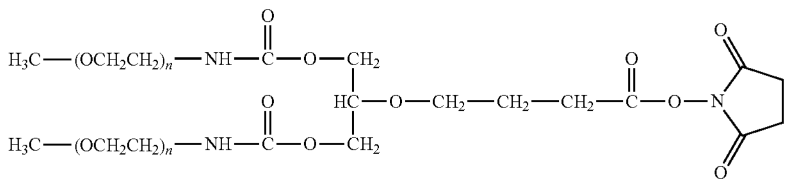

Branched mPEG2-N-Hydroxysuccinimide, 60 kDa

Branched mPEG2-N-hydroxysuccinimide, 60 kDa, stored at −20° C. under argon, was warmed to ambient temperature. The branched mPEG2-N-hydroxysuccinimide (0.326 mg) was dissolved in 32.6 μL of 2 mM HCl to form a branched mPEG2-N-hydroxysuccinimide solution. The branched mPEG2-N-hydroxysuccinimide solution was added to an aliquot of the stock infliximab liquid (164 μg of infliximab) (stock infliximab liquid pH adjusted to 7.0 using conventionals methods) until a ten-fold excess of the branched mPEG2-N-hydroxysuccinimide to infliximab was reached. The pH was tested and adjusted as necessary to ensure a pH of 7.0. The solution reacted for 30 minutes and then a second addition of mPEG2-N-hydroxysuccinimide solution was prepared and added in the same manner as before. To allow for coupling of the branched mPEG2-N-hydroxysuccinimide to infliximab via an amide linkage, the reaction solution was stirred for two hours at room temperature and then overnight (sixteen hours) at 6° C., thereby resulting in a conjugate solution. The reaction was quenched by addition of glycine.

According to SDS-PAGE analysis, approximately 30% of the native was conjugated to PEG. The reaction yielded mostly 1-mers and some 2-mers.

Using this same approach, other conjugates can be prepared using branched mPEG2-N-hydroxysuccinimide having other weight average molecular weights.

Example 16

Radioligand Binding Assay

Conjugates prepared in accordance with the Examples and preceding description were tested for activity based on a radioligand binding assay. The following materials were used: source, Human U937 cells; ligand, 0.028 nM [$^{125}$I] TNF-α; vehicle, 1% 50 mM $NaPO_4$ pH 8.0; incubation time/temperature, three hours at 4° C.; incubation buffer, 50 mM Tris-HCl, pH 7.4, 0.5 mM EDTA at 4° C.; non-specific ligand, 0.04 μM TNF-α; $K_D$, 0.07 nM; $B_{MAX}$, 0.2 pmole/mg protein; specific binding, 60%; quantitation method, radioligand binding; significance criteria, ≥50% of max stimulation or inhibition. Where presented, $IC_{50}$ values were determined by a non-linear, least squares regression analysis using Data Analysis Toolbox™ (MDL Information Systems, San Leandro, Calif.). Where inhibition constants ($K_I$) are presented, the $K_I$ values are calculated using the equation of Cheng and Prusoff (Cheng et al. Biochem. Pharmacol. 22:3099-3108, 1973) using the observed $IC_{50}$ of the tested compound, the concentration of radioligand employed in the assay, and the historical values for the $K_D$ of the ligand (obtained experimentally). Where presented, the Hill coefficient ($n_H$), defining the sloop of the competitive binding curve, was calculated using Data Analysis Toolbox™. Hill coefficients significantly different than 1.0, may suggest that binding displacement does not follow the laws of mass action with a single binding site. Where $IC_{50}$, $K_1$, and/or $n_H$ data are presented without Standard Error of the Mean (SEM), data are insufficient to be quantitative, and the values presented ($IC_{50}$, $K_1$, $n_H$) should be interpreted with caution. Results are provided in Table 4.

TABLE 4

| Activity Based on a Radioligand Binding Assay | | | | | |
|---|---|---|---|---|---|
| Compound ID | Concentration | % Inhibition | $IC_{50}$ | $K_I$ | $n_H$ |
| Conjugate A | 3 nM | 51 | 2.85 ± 0.204 nM | 2.04 ± 0.145 nM | 1.43 ± 0.162 |
| Conjugate B | 11 nM | 52 | 0.850 ± 0.063 nM | 0.607 ± 0.045 nM | 1.76 ± 0.165 |
| Conjugate C | 3 nM | 62 | 1.54 ± 0.178 nM | 1.1 ± 0.127 nM | 1.43 ± 0.098 |
| Conjugate D | 1 nM | 58 | 0.636 ± 0.039 nM | 0.454 ± 0.028 nM | 1.59 ± 0.115 |
| Conjugate E | 10 nM | 50 | 9.87 ± 0.782 nM | 7.05 ± 0.558 nM | 1.65 ± 0.162 |

What is claimed is:

1. A composition comprising:

(i) a conjugate comprising a single water-soluble polymer that is a polyethylene glycol terminally capped with a methoxy group and having a weight-average molecular weight in the range of from about 10,000 daltons to about 100,000 daltons covalently attached, either directly or through a spacer moiety of one to twenty atoms, to an amino group of an amino acid side chain or an N-terminal amine of a full length anti-TNFα antibody that is neither galactosylated nor glycosylated, wherein the one to twenty atoms within the spacer moiety, when present, include the covalent attachment to the amino group of the full length anti-TNFα antibody and atoms derived from a water-soluble polymer reagent used to attach the water-soluble polymer to the full length anti-TNFα antibody; and (ii) a pharmaceutically acceptable excipient, wherein at least about 95% of the conjugates in the composition have a single water soluble polymer attached to the full length anti-TNFα antibody.

2. The composition of claim 1, wherein at least 99% of the conjugates in the composition have a single water soluble polymer attached to the full length anti-TNFα antibody.

3. The composition of claim 1, free of albumin.

4. The composition of claim 2, containing from about 15 to about 95% by weight of the pharmaceutically acceptable excipient.

5. The composition of claim 2, in the form of a powder suitable for reconstitution as a liquid.

6. The composition of claim 5, wherein the powder is a lyophilate.

7. The composition of claim 2, in the form of a liquid.

8. The composition of claim 7, wherein the liquid is a solution or suspension.

9. The composition of claim 2, in unit dosage form.

10. The composition of claim 2, wherein the water-soluble polymer is branched.

11. The composition of claim 2, wherein the water-soluble polymer is linear.

12. The composition of claim 2, wherein the full length anti-TNFα antibody is not a dimer or trimer.

13. The composition of claim 2, wherein the full length anti-TNFα antibody is monovalent.

14. The composition of claim 2, wherein the full length anti-TNFα antibody is not CDR-grafted.

15. The composition of claim 2, wherein the conjugate has the structure:

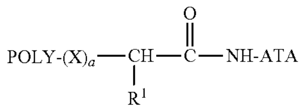

wherein POLY is the water-soluble polymer; (a) is zero or one; X, when present, is the spacer moiety; $R^1$ is H or an organic radical having 1 to 3 carbon atoms; and ATA is the full length anti-TNFα antibody.

16. The composition of claim 2, wherein the conjugate has the structure:

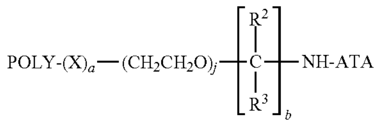

wherein POLY is the water-soluble polymer; X, when present, is the spacer moiety; (a) is either zero or one; (j) is zero or an integer from 1 to about 20; (b) is zero or an integer from 1 to about 10; each $R^2$, when present, is H or an organic radical; each $R^3$, when present, is H or an organic radical; and ATA the full length anti-TNFα antibody.

17. The composition of claim 15, wherein the conjugate has the structure:

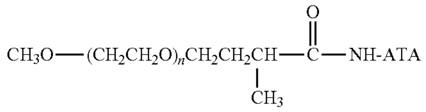

wherein n ranges from about 225 to about 1930.

18. The composition of claim 15, having the structure:

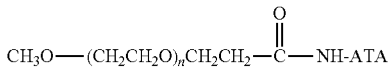

wherein n ranges from about 225 to about 1930.

19. The composition of claim 1, wherein the poly(ethylene glycol) has a weight-average molecular weight in the range of from about 10,000 Daltons to about 85,000 Daltons.

20. The composition of claim 1, wherein the anti-TNFα antibody is either infliximab or adalimumab.

* * * * *